United States Patent
Levy et al.

(10) Patent No.: US 8,845,507 B2
(45) Date of Patent: Sep. 30, 2014

(54) INORGANIC NANOPARTICLES OF HIGH DENSITY TO DESTROY CELLS IN-VIVO

(75) Inventors: Laurent Levy, Paris (FR); Agnes Pottier, Bourg la Reine (FR); Annabelle Rouet, Paris (FR); Julie Marill, Saint Mande (FR); Corinne Devaux, Fontenay le Fleury (FR); Matthieu Germain, Champigny sur Marne (FR)

(73) Assignee: Nanobiotix, Paris (FR)

( * ) Notice: Subject to any disclaimer, the term of this patent is extended or adjusted under 35 U.S.C. 154(b) by 892 days.

(21) Appl. No.: 12/994,162

(22) PCT Filed: Jun. 4, 2009

(86) PCT No.: PCT/EP2009/056880
§ 371 (c)(1),
(2), (4) Date: May 9, 2011

(87) PCT Pub. No.: WO2009/147214
PCT Pub. Date: Dec. 10, 2009

(65) Prior Publication Data
US 2011/0213192 A1 Sep. 1, 2011

Related U.S. Application Data

(60) Provisional application No. 61/060,202, filed on Jun. 10, 2008.

(51) Int. Cl.
*A61N 5/00* (2006.01)
*B82Y 5/00* (2011.01)
*A61K 41/00* (2006.01)

(52) U.S. Cl.
CPC ............... *A61K 41/0038* (2013.01); *B82Y 5/00* (2013.01); *Y10S 977/904* (2013.01)
USPC ................................ 600/1; 424/490; 977/904

(58) Field of Classification Search
USPC .......... 600/1–8; 977/806–808, 904, 911–912; 424/490
See application file for complete search history.

(56) References Cited

U.S. PATENT DOCUMENTS

2007/0217996 A1  9/2007 Levy et al.

FOREIGN PATENT DOCUMENTS

| WO | WO 2005/120590 | 12/2005 |
| WO | WO 2006/138268 | 12/2006 |
| WO | WO 2008/007290 | 1/2008 |
| WO | WO 2008/059419 | 5/2008 |

OTHER PUBLICATIONS

Chen, Y. et al. "Nano neodymium oxide induces massive vacuolization and autophagic cell death in non-small cell lung cancer NCI-H460 cells" *Biochemical and Biophysical Research Communications*, 2005, pp. 52-60, vol. 337, XP-002495930.
Fortin, M.-A. et al. "Polyethylene glycol-covered ultra-small $Gd_2 O_3$ nanoparticles for positive contrast 1.5 T magnetic resonance clinical scanning" *Nanotechnology*, 2007, pp. 1-9, vol. 18, XP-002495929.
Smith, B. W. et al. "Rhenium oxide nanoparticles for the targeted radiotherapy of solid tumors" *Abstracts of Papers American Chemical Society*, Aug. 2004, p. U6, vol. 228, Part 2, XP-008096435.
Tsai, Y. et al. "Novel synthesis of cerium oxide nanoparticles for free radical scavenging" Nanomedicine, 2007, pp. 325-332, vol. 2, No. 3, XP-008096453.
Webb, P. A. "Volume and Density Determinations for Particle Technologists" Retrieved from the Internet: URL: http://www.micromeritics.com/pdf/app_articles/density_determinations.pdf>, Feb. 2001, pp. 1-16, XP-002495931.
Written Opinion in International Application No. PCT/EP2009/056880, Dec. 7, 2009, pp. 1-8.

*Primary Examiner* — John Lacyk
(74) *Attorney, Agent, or Firm* — Saliwanchik, Lloyd & Eisenschenk

(57) ABSTRACT

The present application relates to novel excitable particles which can be used in the health sector. It more particularly relates to particles which can generate electrons and/or high energy photon when excited by ionizing radiations such as X-Rays, γ-Rays, radioactive isotope and/or electron beams, and to the uses thereof in health, in particular in human health. The inventive particles are made of an inorganic material comprising oxygen, in particular an oxide, said material having an adequate density, and can be activated in vitro, ex vivo, or in vivo, by controllable external excitation, in order to disturb, alter or destroy target cells, tissues or organs. The invention also relates to methods for the production of said particles, and to pharmaceutical or medical device compositions containing same.

22 Claims, 18 Drawing Sheets

A)

B)

| | density | Product | HCT116 SF2 (%) | HT29 SF4 (%) |
|---|---|---|---|---|
| Negative control ($H_2O$) | | | 18 | 11 |
| $HfO_2$ (example 2) | <7 | 400 µM | 18 | 8 |
| $HfO_2$ (example 1) | >7 | 400 µM | 12 | 3,5 |

| sample | Without HMP coating | | | With HMP coating | | |
|---|---|---|---|---|---|---|
| | Before filtration (concentration in g/L) | After filtration (concentration in g/L) | filtration yield (%) | Before filtration (concentration in g/L) | After filtration (concentration in g/L) | filtration yield (%) |
| $CeO_2$-D example 10 e) $H_2O$ pH7 | 5.3 | 0 | 0 | 5.3 | 5.1 | 96 |
| $TiO_2$-5nm example 10 d) $H_2O$ pH7 | 6.7 | 0 | 0 | 6.7 | 6.7 | 100 |
| $TiO_2$-5nm example 10 d) Glucose 5% pH7 | 4.5 | 0 | 0 | 4.5 | 4.4 | 98 |
| $HfO_2$-Ref. example 3 $H_2O$ pH7 | 5.7 | 0 | 0 | 5.7 | 5.7 | 100 |
| $HfO_2$-Ref. example 3 Glucose 5% pH7 | 5.7 | 0 | 0 | 5.7 | 5.6 | 98 |

INORGANIC NANOPARTICLES OF HIGH DENSITY TO DESTROY CELLS IN-VIVO

CROSS-REFERENCE TO RELATED APPLICATIONS

This application is the U.S. national stage application of International Patent Application No. PCT/EP2009/056880, filed Jun. 4, 2009, which claims the benefit of U.S. Provisional Patent Application No. 61/060,202, filed Jun. 10, 2008.

FIELD OF THE INVENTION

The present application relates to novel excitable particles which can be used in the health sector. It more particularly relates to particles which can generate electrons and/or high energy photons when excited by ionizing radiations such as X-Rays, gamma-Rays (γ-Rays), radioactive isotope and/or electron beams, and to the uses thereof in health, in particular in human health. The inventive particles are made of an inorganic material comprising oxygen, in particular an oxide, said material having an adequate density, and can be activated in vitro, ex vivo, or in vivo, by controllable external excitation, in order to disturb, alter or destroy target cells, tissues or organs. The invention also relates to methods for the production of said particles, and to pharmaceutical compositions containing same.

BACKGROUND

Radiations of various forms such as X-Rays, gamma-Rays, UV-Rays, laser light, microwaves, electron beams as well as particle beams of, for example neutrons, and protons, have been used to treat cancer related issues. Some of said radiations have been used in such applications, in combination with radiation sensitive molecules. Electromagnetic and ionizing radiations are indeed capable of breaking the DNA molecule of the cell, thereby preventing said cell from growing and dividing. This effect is mainly due to damages created by electrons and/or high energy photons (energy higher than 2 KeV) emitted after ionization.

The term "Ionizing radiations" refers to highly-energetic particles or waves that can detach (ionize) at least one electron from an atom or molecule. Ionizing ability depends on the energy of individual particles or waves, and not on their number. A large flood of particles or waves will not, in the most-common situations, cause ionization if the individual particles or waves are insufficiently energetic.

Examples of ionizing radiations are energetic beta particles, photons, neutrons, electron and alpha particles. The ability of light waves (photons) to ionize an atom or molecule varies across the electromagnetic spectrum. X-Rays and gamma-Rays will ionize almost any molecule or atom; far ultraviolet light will ionize many atoms and molecules; near ultraviolet and visible light are ionizing very few molecules; microwaves and radio waves are non-ionizing radiations.

WO 2005/120590 describes a particle comprising (i) a nucleus comprising a first inorganic compound absorbing X-Rays and emitting UV-visible energy, and (ii) a second, inorganic or organic compound, absorbing UV-visible energy and producing free radicals on contact with water or oxygen. The activated particles convert the surrounding oxygen to free radicals which are highly reactive species producing irreversible damage in cells.

US 2007/0274909 relates to nanoparticles for use in imaging or in radiation treatment of biological material, comprising a VUV or UV-C emitting material which absorbs high energy radiation and emits VUV or UV-C radiation. The VUV or UV-C emitting materials described in this specification are intentionally or non-intentionally, but systematically, doped with an activator the aim of which is to allow the described VUV or UV-C radiation emission. Doping agents may however be associated with an increased toxicity depending on their localization in the particle or on their solubility in the dispersion medium.

U.S. Pat. No. 6,955,639 describes a method of enhancing X-Rays radiation effects using metal, in particular gold, nanoparticles.

Inventors herein provide new and powerful nanoparticles, which are easier and cheaper to prepare than those described in the art, but more importantly and surprisingly able to achieve a very efficient alteration or destruction of target cells in combination with ionizing radiations, as herein demonstrated.

Another feature exhibited by the herein described nanoparticles is their ability to remain inside the tumor for several days allowing reducing the number of nanoparticles and/or nanoparticles aggregates injections to a minimum, in the context of a complete radiotherapy treatment.

SUMMARY OF THE INVENTION

Inventors have now discovered that it is possible to efficiently disturb, alter or destroy target cells, tissues or organs, in particular abnormal cells or tissues, herein defined as benign cells or tissues, or diseased cells or tissues, such as pre-malignant or malignant cells (cancerous cells) or tissues (tumors), possibly located deep in the body, while limiting damages to the surrounding healthy tissues, using a nanoparticle made of an inorganic material comprising oxygen (in other words, prepared with a single inorganic material), in particular an oxide, the density of which is of at least 7 g/cm$^3$, preferably above 7 g/cm$^3$, in particular, for a nanoparticle made of an oxide, above 7 g/cm$^3$ and below 15 g/cm$^3$.

Such nanoparticles do not require the presence of an additional distinct compound or material to generate the desired therapeutic effect. In particular, the herein described nanoparticles are able to directly convert the incoming radiation into an efficient emission of electrons and/or high energy photons which is responsible for the subsequent therapeutic effect.

Contrary to the nanoparticles described in WO 2005/120590 and US 2007/0274909, the present nanoparticles do not require the presence of two distinct compounds, one of which is necessary to convert X-Rays into UV-visible energy. In particular, the present nanoparticles do not comprise an inorganic compound the aim of which is, as a first compound, to absorb X-Rays and convert them into UV-visible energy absorbed by a second compound which is, in turn, responsible for irreversible damages in cells. These nanoparticles are also not doped or design to specifically emit light in the UV region.

Compared to metal nanoparticles, the present nanoparticles offer the advantage of exhibiting hydroxyl (OH) groups on their surfaces which are responsible for the compatibility with any polar environment, in a large range of pH.

Compared to metal nanoparticles, the present nanoparticles, in particular the nanoparticles made of an oxide, further offer the advantage of being easier to prepare. Biocompatible suspensions with a high concentration of nanoparticles or nanoparticles aggregates can be obtained with a method as herein described.

The synthesis process does not require the use of a reducing agent and/or of a sequestering (complexing) agent to prevent detrimental aggregation of the prepared particles. In the herein described methods, the addition of a sequestering (complexing) agent to the above mentioned suspensions is only optional.

Hence, synthesis process generally includes (simultaneously or sequentially): precipitation of a chemical element in a polar medium, crystallisation of said chemical element (oxygen is part of the inorganic material structure) and stabilisation (if needed) in a physiological medium.

The present nanoparticles further do not require a targeting molecule to concentrate into the target cells or tissues.

The Enhanced Permeation and Retention ("EPR") effect is indeed responsible for passive accumulation into the tumor mass, after a given time following injection by the intravenous route (one possible route of administration) of the nanoparticles. It has indeed been observed that the tumor vessels are quite distinct from normal capillaries and that their vascular "leakiness" encourages selective extravasation of nanoparticles not usual in normal tissues. The lack of effective tumour lymphatic drainage prevents clearance of the penetrant nanoparticles and promotes their accumulation. The present nanoparticles are thus able to successfully target primary as well as metastatic tumors after intravenous administration.

The present nanoparticles can also be advantageously administered through intratumoral route, as demonstrated in the experimental section.

The present nanoparticles or nanoparticles aggregates are however advantageously covered with a biocompatible coating allowing the nanoparticle or nanoparticle aggregate stability between pH 6.5 and 7.5 in a physiological fluid as further described herein below.

It is a thus further advantage of the present invention to provide nanoparticles that are not noxious by themselves but can be safely employed, in appropriate conditions, to functionally disturb, alter or destruct target cells, in particular cancerous cells. The desired therapeutic effect of nanoparticles is indeed strictly dependant from their excitation, said excitation being generated by the ionizing radiation source which is itself advantageously controlled, in terms of quality and quantity, and used in a targeted, i.e., localized, way, by the man of the art.

The present invention thus describes a novel class of particles which can be used, if appropriate in a targeted manner, in any animal, preferably in a mammal, even more preferably in a human. The inventive particles can be used in any type of tissue or organ, superficial or deep. In particular, the present invention describes activable particles which can induce a cell alteration or destruction in vitro, ex vivo or in vivo when said cells are exposed to ionizing radiations such as in particular X-Rays, gamma-rays, radioactive isotopes, ion beams and/or electron beams.

The strategy applied consists in converting incoming ionizing radiations mainly into an efficient emission of electrons and/or high energy photons which is responsible for the therapeutic effect. Such a result is obtained by using the present nanoparticles made of an inorganic material comprising oxygen, the density of which is of at least 7 $g/cm^3$, preferably above 7 $g/cm^3$, in particular, for a nanoparticle made of an oxide, above 7 $g/cm^3$ and below 15 $g/cm^3$.

The present nanoparticles are excited or activated by absorption of energy from ionizing radiations. Such absorption leads to a subsequent cascade of phenomena leading to the alteration or death of the target cell. Among those phenomena, the emission of electrons and/or high energy photons is predominant and critical in the context of the present invention.

Inventors herein demonstrate the efficiency of an inorganic material comprising oxygen, the density of which is of at least 7 $g/cm^3$, preferably above 7 $g/cm^3$, in particular, for a nanoparticle made of an oxide, above 7 $g/cm^3$ and below 15 $g/cm^3$, in obtaining the desired therapeutic effect, consisting of the alteration or destruction of a target cell, tissue or organ, such as a malignant cell or tissue.

The present invention relates to products or compounds, herein nanoparticles or nanoparticles aggregates, made of an inorganic material comprising oxygen, the density of said inorganic material being of at least 7 $g/cm^3$, preferably above 7 $g/cm^3$, in particular, for a nanoparticle made of an oxide, above 7 $g/cm^3$ and below 15 $g/cm^3$. Methods of preparing such compounds are herein disclosed.

It is an object of the present invention to use a nanoparticle or nanoparticle aggregate according to the present invention to alter, destroy or eliminate a target cell, tissue or organ.

A particular embodiment herein disclosed relates to the use of a nanoparticle or nanoparticle aggregate to prepare a pharmaceutical composition intended to alter, destroy or eliminate target cells in an animal when said cells are exposed to ionizing radiations as herein defined, wherein the nanoparticle is made of an inorganic material comprising oxygen, the density of said inorganic material being of at least 7 $g/cm^3$, preferably above 7 $g/cm^3$, in particular, for a nanoparticle made of an oxide, above 7 $g/cm^3$ and below 15 $g/cm^3$, and to the corresponding method of treatment.

Products according to the present invention, in particular nanoparticle or nanoparticle aggregates, for use in the treatment of cancer, are in particular herein disclosed.

Another embodiment is based on a composition, in particular a pharmaceutical composition for use in therapy or diagnostic, comprising a product such as defined hereinabove or which can be obtained by the afore mentioned method. Such a composition is preferably in the form of an injectable formulation.

Herein disclosed is a pharmaceutical composition, in particular, as will be apparent from the all description, a pharmaceutical composition intended to alter or destroy target cells in a mammal when said cells are exposed to ionizing radiations, said pharmaceutical composition comprising a nanoparticle or nanoparticle aggregate and a pharmaceutically acceptable carrier or excipient, wherein the nanoparticle is made of an inorganic material comprising oxygen, the density of said inorganic material being of at least 7 $g/cm^3$, preferably above 7 $g/cm^3$, in particular, for a nanoparticle made of an oxide, above 7 $g/cm^3$ and below 15 $g/cm^3$, and wherein the nanoparticle or nanoparticles aggregate is preferably covered with a biocompatible coating.

Another embodiment relates to the use of a nanoparticle or nanoparticle aggregate according to the present invention to prevent or treat a cancer or to alleviate the symptoms of a cancer in an animal, when said nanoparticle or nanoparticle aggregate is exposed to radiations, in particular to ionizing radiations as herein defined.

The present disclosure in particular encompasses a method for preventing or treating a cancer or for alleviating the symptoms of a cancer in a subject, the subject being an animal, in particular a mammal, preferably a human, by administering a nanoparticle or nanoparticles aggregate according to the present invention, or a composition comprising such a nanoparticle or nanoparticle aggregate, to the subject, and exposing said subject to radiations, in particular to ionizing radiations.

In another aspect, the present disclosure provides kits comprising any one or more of the herein-described products, i.e., nanoparticles, nanoparticle aggregates, and compositions, together with a labeling notice providing instructions for using the product(s).

Microtomography has been performed on tumor, 2 and 15 days following injection.

Figure 2:
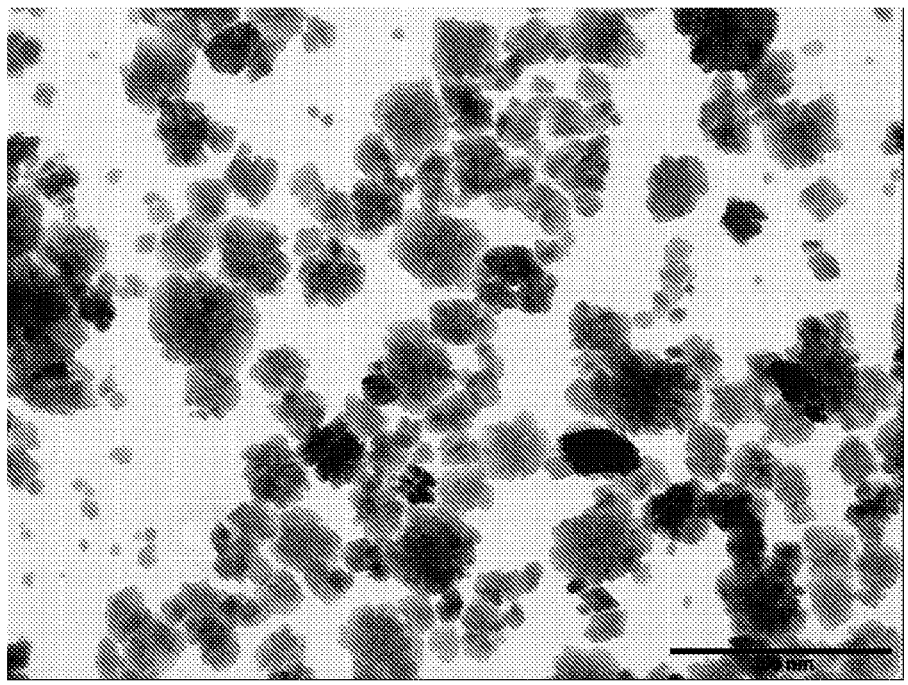
Figure 2:
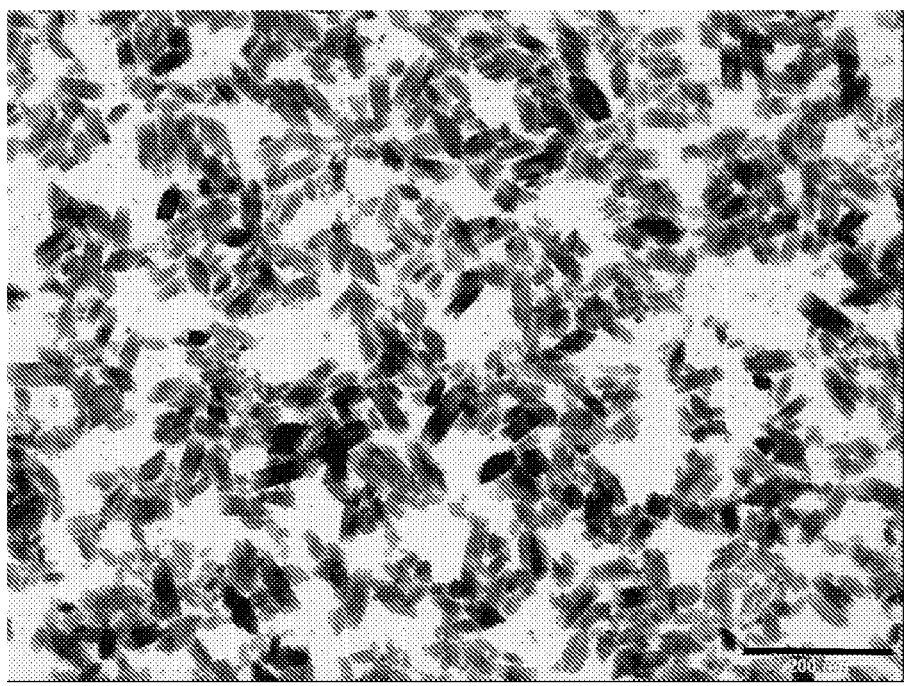

FIGS. 2A and 2B are Transmission Electronic Microscopy (TEM) images of $HfO_2$ nanoparticles and nanoparticle aggregates giving a qualitative characterization of the nanoparticles shape (scale bar=200 nm). JEOL 100 CX is used for analysis.

FIG. 2A shows nanoparticles and also aggregates formed with nanoparticles, both being essentially spherical in shape.

FIG. 2B shows nanoparticles prepared in a different way and aggregates formed with said nanoparticles, both being essentially elongated in shape.

Figure 3:
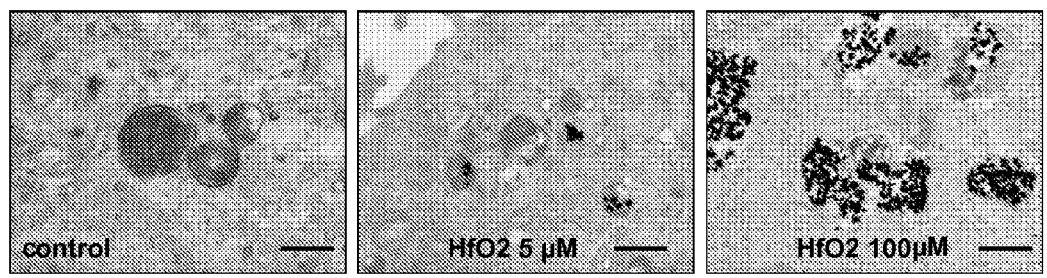

FIG. 3 shows Transmission Electronic Microscopy (TEM) pictures of nanoparticles internalized in cells. HCT116 cultures were treated 24 h without (control), and with 5 and 100 µM of biocompatible suspension of $HfO_2$ nanoparticles or nanoparticles aggregates (scale bar 500 nm).

Nanoparticles were uptaken through the endosomes. The TEM study clearly revealed that nanoparticles enter cells through the endosomes in a concentration dependent manner. Nanoparticles can enter or penetrate the cell, in an aggregated or individualized way, depending on their design and/or concentration.

Figure 4:
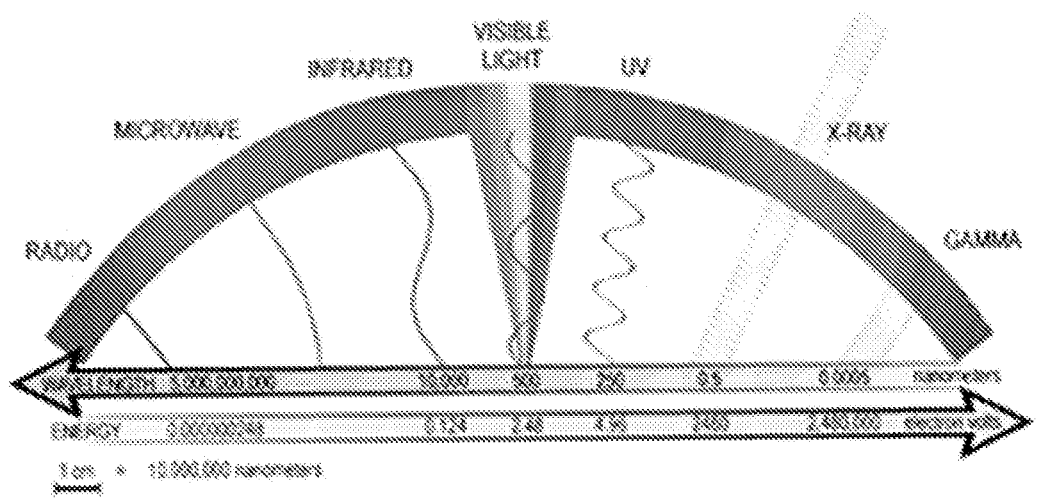

FIG. 4: Electromagnetic spectrum with ionizing radiations highlighted.

FIG. 5A shows the grey level or contrast value of biocompatible suspension of $HfO_2$ nanoparticles and nanoparticles aggregates as a function of their concentration:

$HfO_2$ with density>7: circles dots
$HfO_2$ with density<7: cross dots

Analyses were performed using X-Ray microtomograph (Skyscan 1076) operating with a source voltage of 50 kV.

Figures 5, 5B:
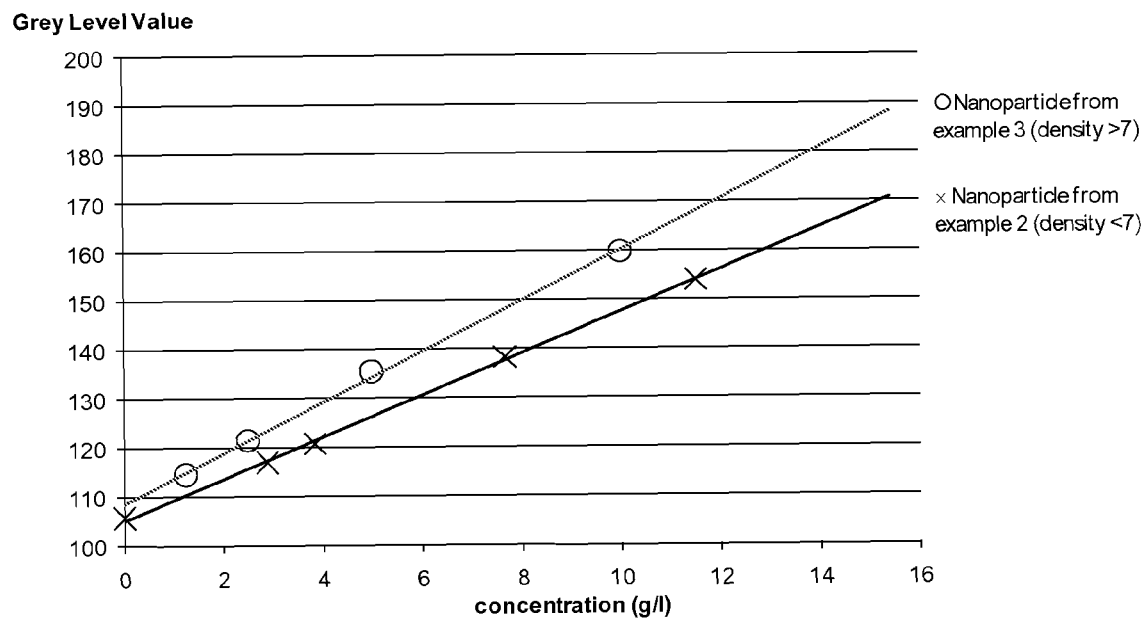

For a given concentration, the highest the grey level of the nanoparticles or nanoparticles aggregates (directly related to their absorption rate or capacity), the highest is the nanoparticles or nanoparticles aggregates ability to increase the radiation induced cell death, as shown in FIG. 5B.

FIG. 5B shows clonogenic survival assay using biocompatible $HfO_2$ nanoparticles or nanoparticles aggregates incubated with two distinct human colon carcinoma cell lines at 400 µM, compared to control.

$SF_x$ (Surviving Fraction under X grays) is determined after an irradiation dose of 2 Gy in the radio sensitive cell line HCT116 and after an irradiation dose of 4 Gy in the radio resistant HT29 cell line, using a 200 keV X-Rays irradiation source (Tube Comet MXR-225/22-200 kV/15 mA/0.2 mm Cu). Mean values are generated from 2 different experiments.

Figure 6:
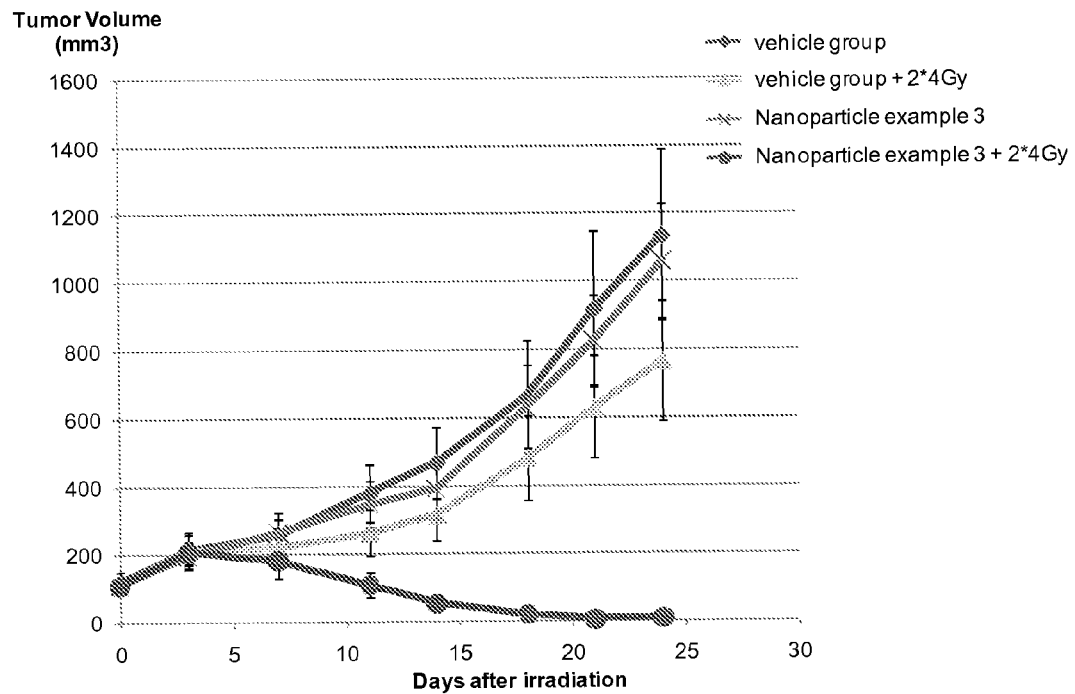

FIG. 6: a biocompatible suspension comprising $HfO_2$ nanoparticles and/or nanoparticle aggregates has been intra-tumorously injected to Swiss nude mice bearing HCT116 tumors (injection volume between 20% and 50% of tumor volume). The tumors of said mice have further been locally irradiated (2 sessions, also herein identified as 2 fractions, of 4 Gy; circle dots) with an applicator coupled to an irradiation source used in an external way [curietherapy device Iridium-192 source].

The same biocompatible suspension has been administered to a control group of mice (injection volume between 20% and 50% of tumor volume). Said control group was not irradiated (crossed dots).

The above described groups of mice are compared to vehicle treated mice submitted (Triangle dots) or not (losange dots) to radiotherapy. Tumor volume is monitored in each group twice a week during 25 days following irradiation.

Figure 7:
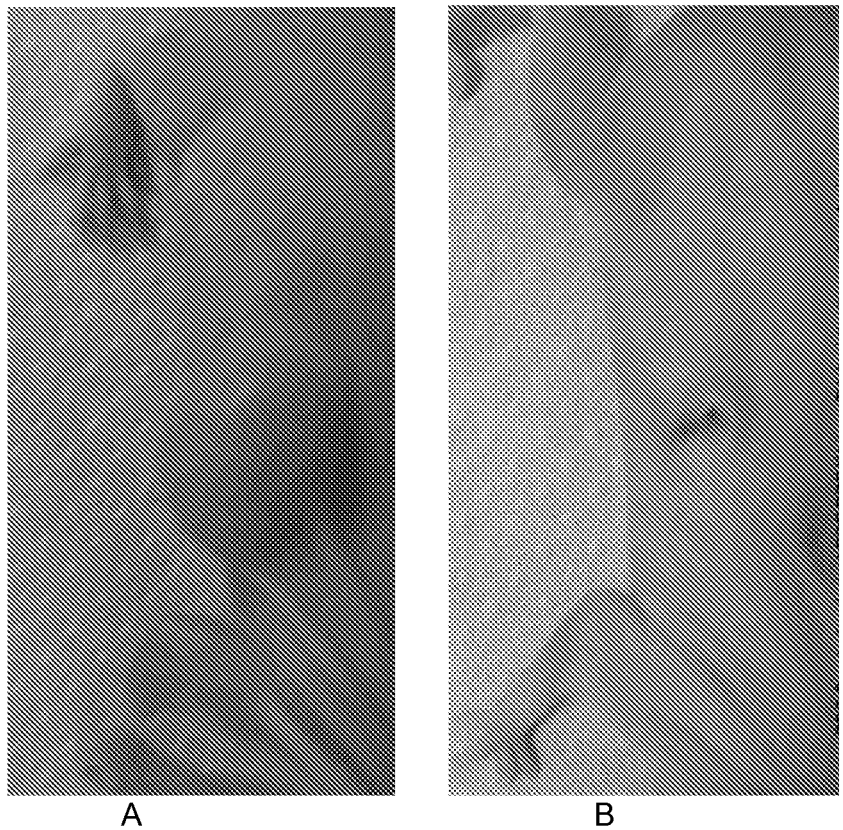

FIG. 7 shows pictures of mice bearing HCT116 tumor cells, 21 days after irradiation:

FIG. 7A: mice treated with irradiation after intra tumoral injection of a vehicle (no particles)

Figure 8:
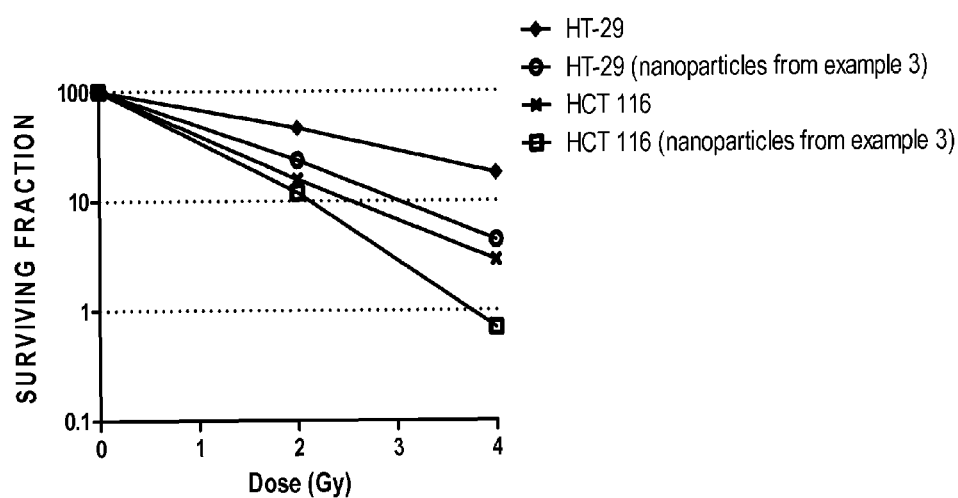

FIG. 7B: mice treated with irradiation after intra tumoral injection of nanoparticles FIG. 8 shows clonogenic survival assays using HCT116 (radio sensitive model) and HT29 (radio resistant model) cancer cells irradiated using a 200 keV X-Rays generator (Tube Comet MXR-225/22-200 kV/15 mA/0.2 mm Cu), in the absence (negative control) or in the presence of 400 µM of $HfO_2$ nanoparticles or nanoparticle aggregates. Irradiation dose varies from 0 to 4 Gy.

Figure 9:
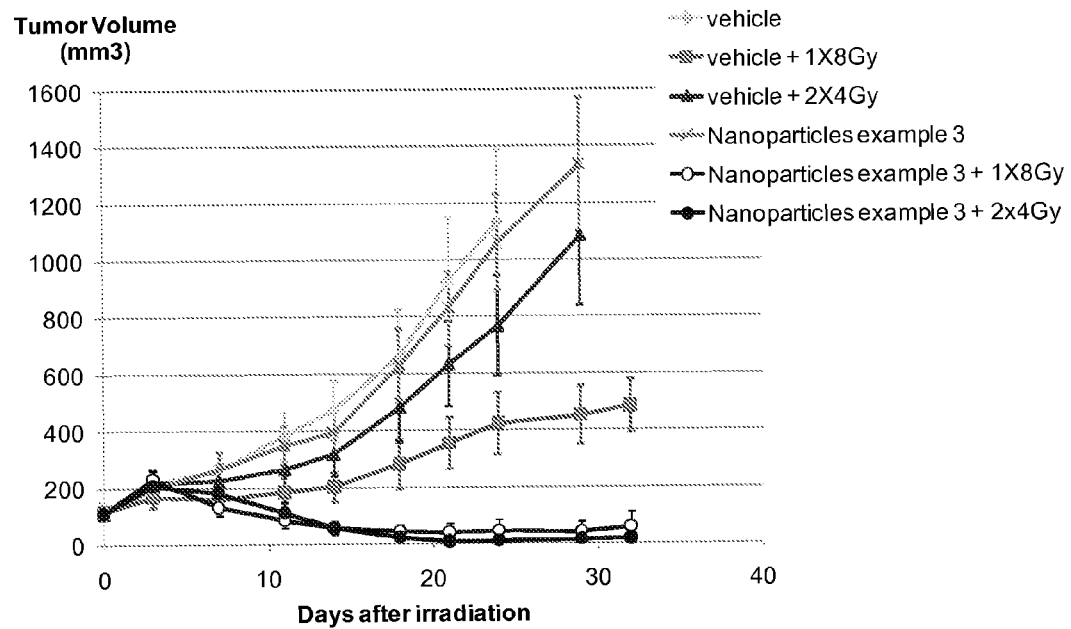

Negative control with HCT116: cross dots
Nanoparticles with HCT116: square dots
Negative control with HT29: losange dots
Nanoparticle with HT29: circle dots FIG. 9 shows HCT116 tumor volumes evolution after intra tumoral injection of a biocompatible suspension of $HfO_2$ nanoparticles or nanoparticle aggregates followed by a 2×4 Gy or a 1×8 Gy irradiation of the tumor with an applicator coupled to an external irradiation using curietherapy device Iridium-192 source.

Mean values are calculated from 8 Swiss nude mice.

Figure 10:
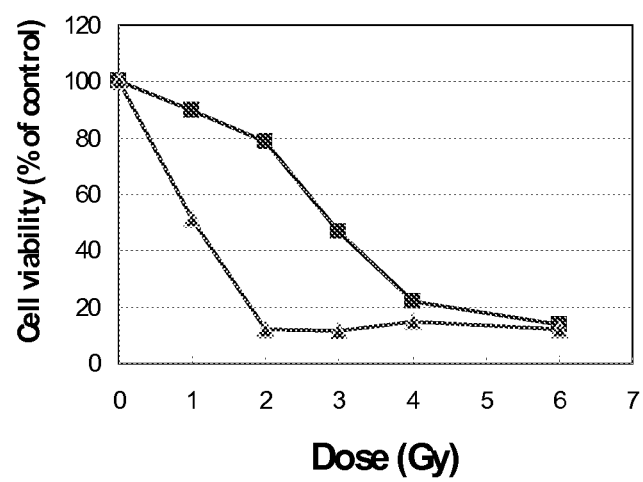

Control group with injected vehicle (no irradiation, no nanoparticles): losange dots Group with injected nanoparticles (no irradiation): crossed dots Group with injected vehicles and submitted to a 1×8 Gy irradiation (no nanoparticles): square dots Group with injected vehicles and submitted to a 2×4 Gy irradiation (no nanoparticles): triangle dots Group with injected nanoparticles and submitted to a 1×8 Gy irradiation: open circle dots Group with injected nanoparticles and submitted to 2×4 Gy irradiation: circle dots FIG. 10 shows cell viability measured after a 24 h-treatment period with or without $HfO_2$ nanoparticles or nanoparticles aggregates (concentration 800 µM). Irradiation doses vary from 0 to 6 Gy. WST-1 kit is used to read viability. Each dot is the mean value of 3 experiments.

Figure 11A:
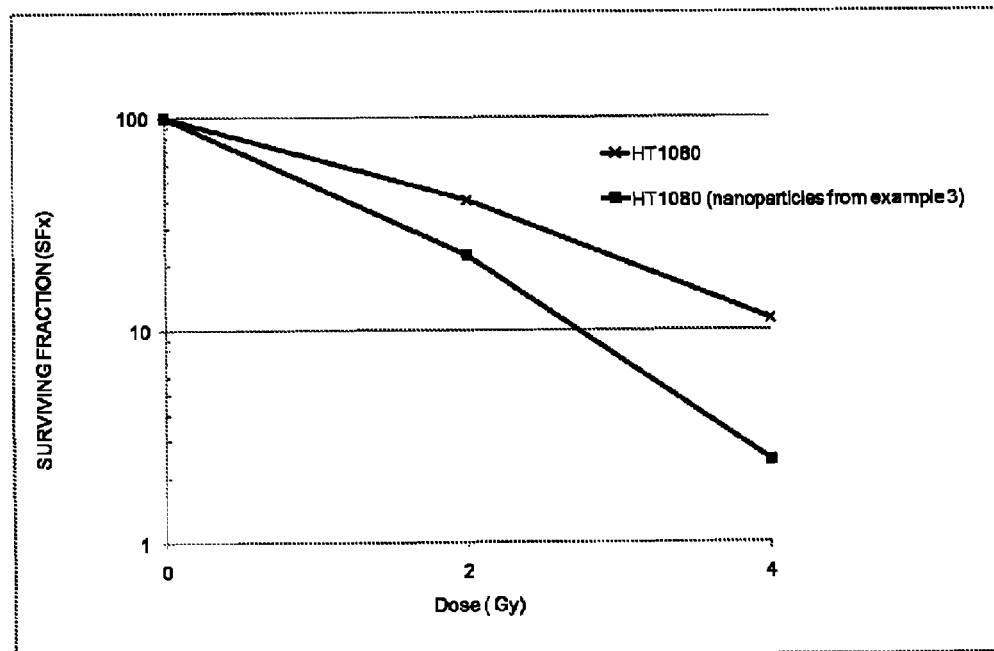

With nanoparticles and irradiation: triangle dots
Without nanoparticles and with irradiation: square dots FIG. 11A shows clonogenic survival assays using HT1080 (fibrosarcoma radio resistant model) cancer cells irradiated using a 200 keV X-Rays generator (Tube Comet MXR-225/22-200 kV/15 mA/0.2 mm Cu) in the absence (negative control) or in the presence of 400 µM of $HfO_2$ nanoparticles or nanoparticle aggregates.

Figure 11B:
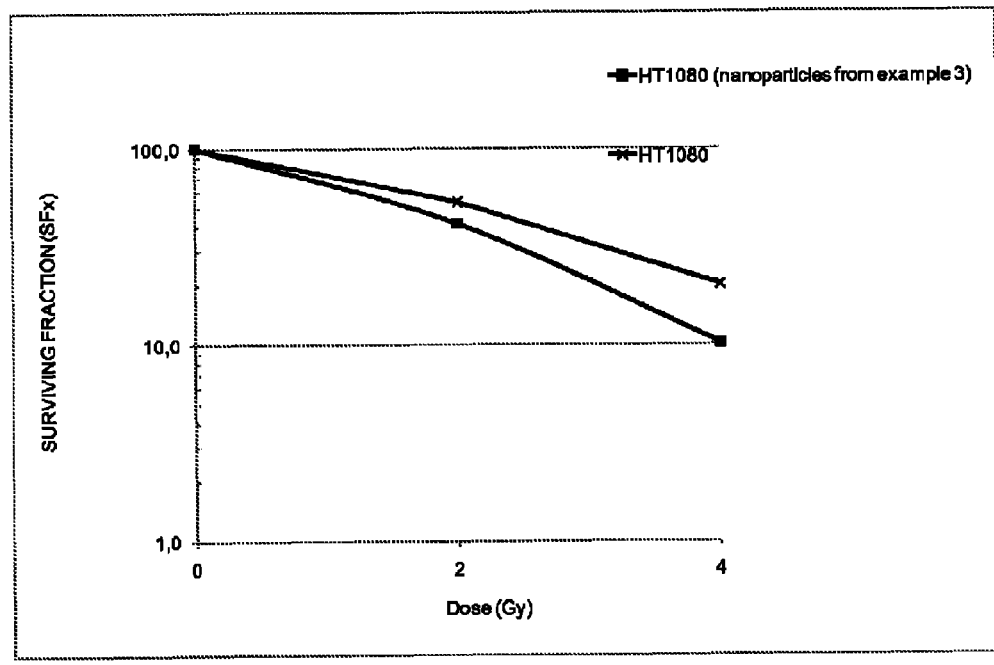

Irradiation dose varies from 0 to 4 Gy.
Negative control with HT1080: cross dots
Nanoparticles with HT1080: square dots FIG. 11B shows clonogenic assays using HT1080 (fibrosarcoma radio resistant model) cancer cells irradiated using a Cobalt 60 source, in the absence (negative control) or in the presence of 400 µM of $HfO_2$ nanoparticles or nanoparticle aggregates. Irradiation dose varies from 0 to 4 Gy.

Negative control with HT1080: cross dots
Nanoparticles with HT1080: Square dots

Similar clonogenic assays were performed on "human fibroblast cells" (non cancerous cells) as a control, using nanoparticles, and showed no or very moderate effect. The results obtained when comparing the respective reaction of cancer and normal cells under irradiation reveal a high benefice over risk ratio.

Figure 12A:
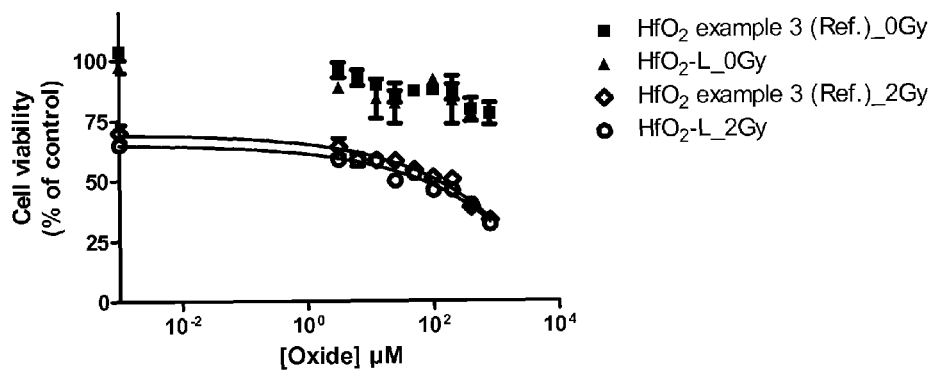

FIG. 12A shows the cell viability (% of control) after a 2 Gy irradiation using $HfO_2$ nanoparticles or nanoparticle aggregates (400 µM) with density of 7.4 g/cm³ (example 10a)).

Figure 12B:
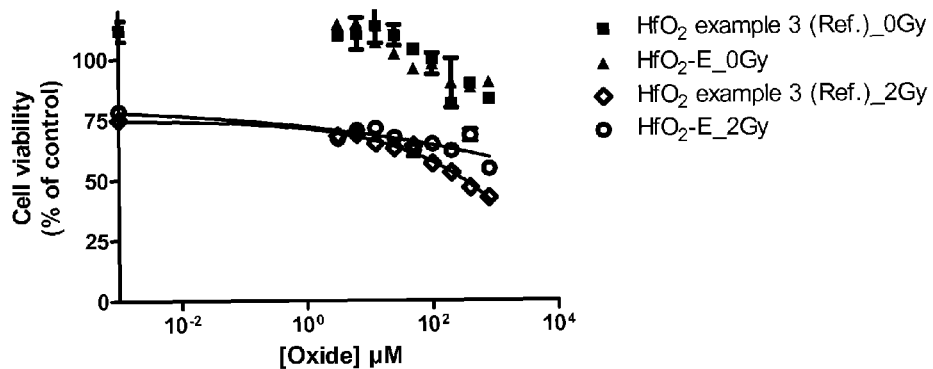

With nanoparticles ($HfO_2$-Ref./example 3/d=8.3) and without irradiation: filled square dots With nanoparticles ($HfO_2$-Ref./example 3/d=8.3) and with irradiation: open losange dots With nanoparticles ($HfO_2$-L d=7.4) and without irradiation: filled triangle dots With nanoparticles ($HfO_2$-L d=7.4) and with irradiation: open circle dots FIG. 12B shows the cell viability (% of control) after a 2 Gy irradiation using $HfO_2$ nanoparticles or nanoparticle aggregates (400 µM) with density of 6.8 g/cm³ (example 10a)).

Figure 12C:
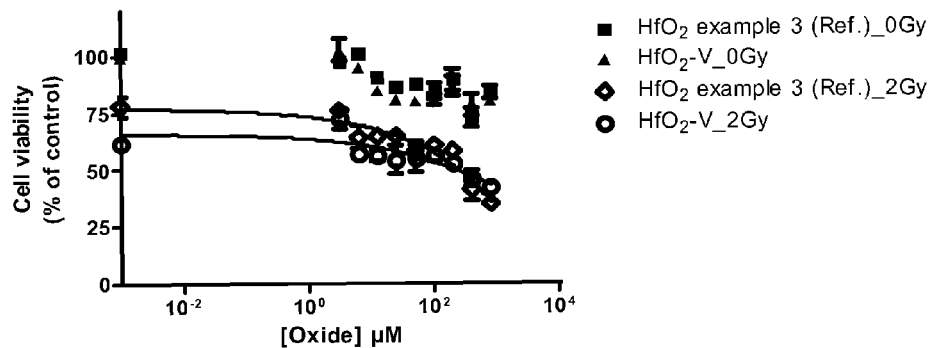

With nanoparticles ($HfO_2$-Ref./example 3/d=8.3) and without irradiation: filled square dots With nanoparticles ($HfO_2$-Ref./example 3/d=8.3) and with irradiation: open losange dots With nanoparticles ($HfO_2$-E d=6.8) and without irradiation: filled triangle dots With nanoparticles ($HfO_2$-E d=6.8) and with irradiation: open circle dots FIG. 12C shows the cell viability (% of control) after a 2 Gy irradiation using $HfO_2$ nanoparticles or nanoparticle aggregates (400 µM) with density of 6.7 g/cm³ (example 10a)).

Figure 12D:
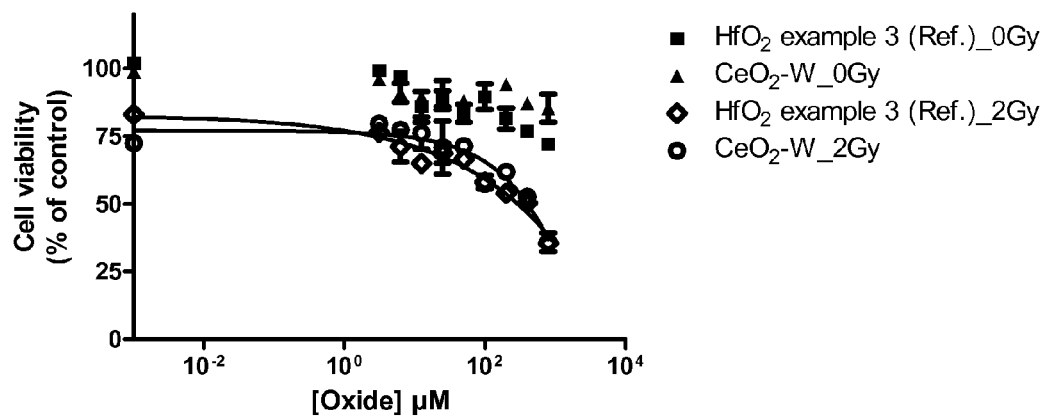

With nanoparticles ($HfO_2$-Ref./example 3/d=8.3) and without irradiation: filled square dots With nanoparticles ($HfO_2$-Ref./example 3/d=8.3) and with irradiation: open losange dots With nanoparticles ($HfO_2$-V d=6.7) and without irradiation: filled triangle dots With nanoparticles ($HfO_2$-V d=6.7) and with irradiation: open circle dots FIG. 12D shows the cell viability (% of control) after a 2 Gy irradiation using $CeO_2$ nanoparticles or nanoparticle aggregates (400 µM) with density of 7.1 g/cm³ (example 10b)).

Figure 12E:
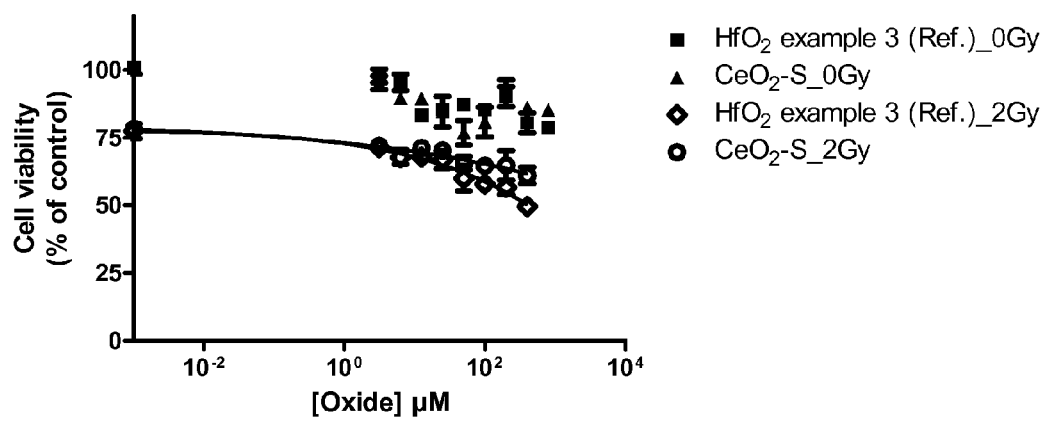

With nanoparticles ($HfO_2$-Ref./example 3/d=8.3) and without irradiation: filled square dots With nanoparticles ($HfO_2$-Ref./example 3/d=8.3) and with irradiation: open losange dots With nanoparticles ($CeO_2$-W d=7.1) and without irradiation: filled triangle dots With nanoparticles ($CeO_2$-W d=7.1) and with irradiation: open circle dots FIG. 12E shows the cell viability (% of control) after a 2 Gy irradiation using $CeO_2$ nanoparticles or nanoparticle aggregates (400 µM) with density of 6.5 g/cm³ (example 10b)).

Figure 12F:
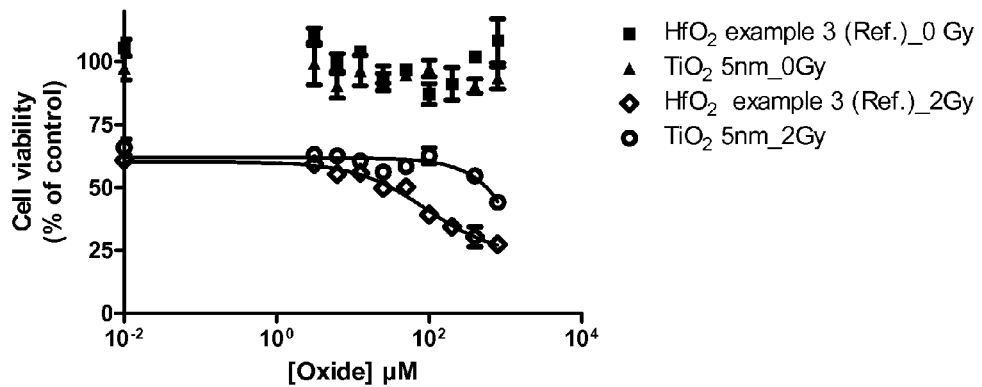

With nanoparticles ($HfO_2$-Ref./example 3/d=8.3) and without irradiation: filled square dots With nanoparticles ($HfO_2$-Ref./example 3/d=8.3) and with irradiation: open losange dots With nanoparticles ($CeO_2$-S d=6.5) and without irradiation: filled triangle dots With nanoparticles ($CeO_2$-S d=6.5) and with irradiation: open circle dots FIG. 12F shows the cell viability (% of control) after a 2 Gy irradiation using $TiO_2$ nanoparticles or nanoparticle aggregates (400 µM) with density of 3.9 g/cm³ (example 10d)).

Figure 12G:
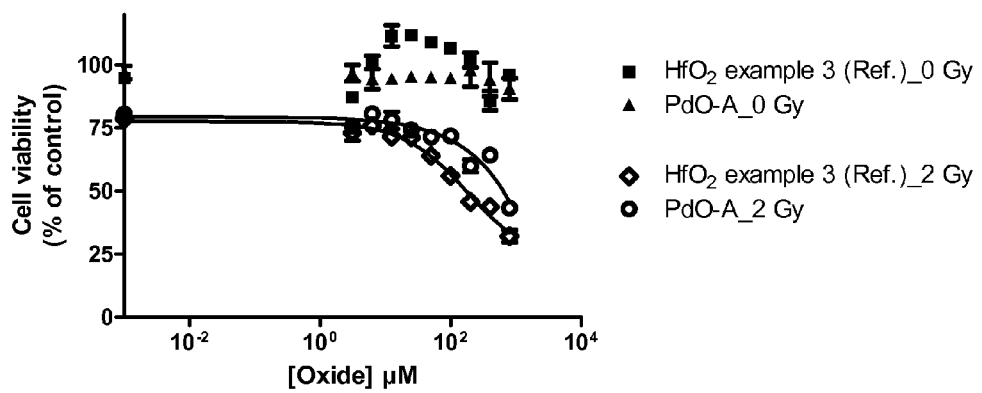

With nanoparticles ($HfO_2$-Ref./example 3/d=8.3) and without irradiation: filled square dots With nanoparticles ($HfO_2$-Ref./example 3/d=8.3) and with irradiation: open losange dots With nanoparticles ($TiO_2$-5 nm d=3.9) and without irradiation: filled triangle dots With nanoparticles ($TiO_2$-5 nm d=3.9) and with irradiation: open circle dots FIG. 12G shows the cell viability (% of control) after a 2 Gy irradiation using PdO nanoparticles or nanoparticle aggregates (400 µM) with density of 7.9 g/cm³ (example 10e)).

Figure 12H:
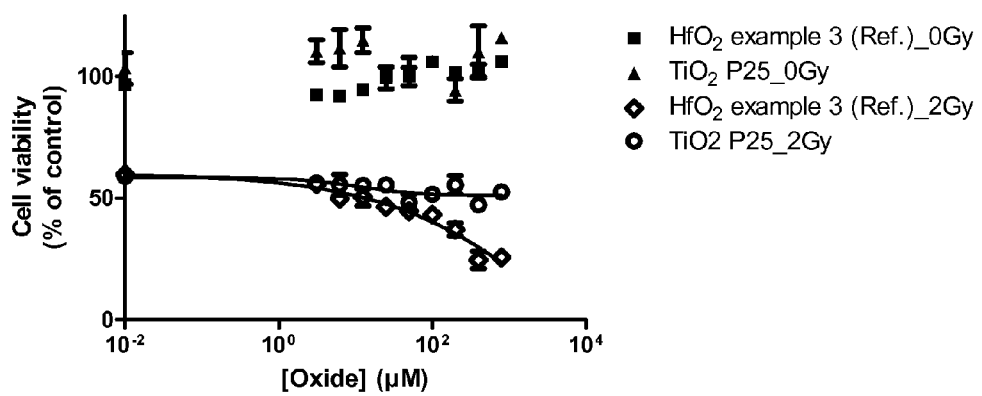

With nanoparticles ($HfO_2$-Ref./example 3/d=8.3) and without irradiation: filled square dots With nanoparticles ($HfO_2$-Ref./example 3/d=8.3) and with irradiation: open losange dots With nanoparticles (PdO-A d=7.9) and without irradiation: filled triangle dots With nanoparticles (PdO-A d=7.9) and with irradiation: open circle dots FIG. 12H shows the cell viability (% of control) after a 2 Gy irradiation using $TiO_2$ nanoparticles or nanoparticle aggregates (400 µM) with density of 3.8 g/cm³ (example 10e)).

Figure 12I:
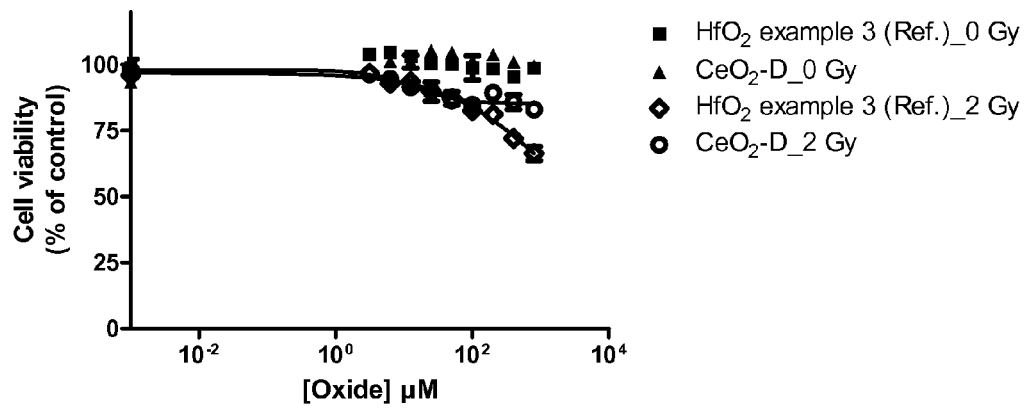

With nanoparticles ($HfO_2$-Ref./example 3/d=8.3) and without irradiation: filled square dots With nanoparticles ($HfO_2$-Ref./example 3/d=8.3) and with irradiation: open losange dots With nanoparticles ($TiO_2$-P25 d=3.8) and without irradiation: filled triangle dots With nanoparticles ($TiO_2$-P25 d=3.8) and with irradiation: open circle dots FIG. 12I shows the cell viability (% of control) after a 2 Gy irradiation using $CeO_2$ nanoparticles or nanoparticle aggregates (400 µM) with density of 6.6 g/cm³ (example 10e)).

Figure 12J:
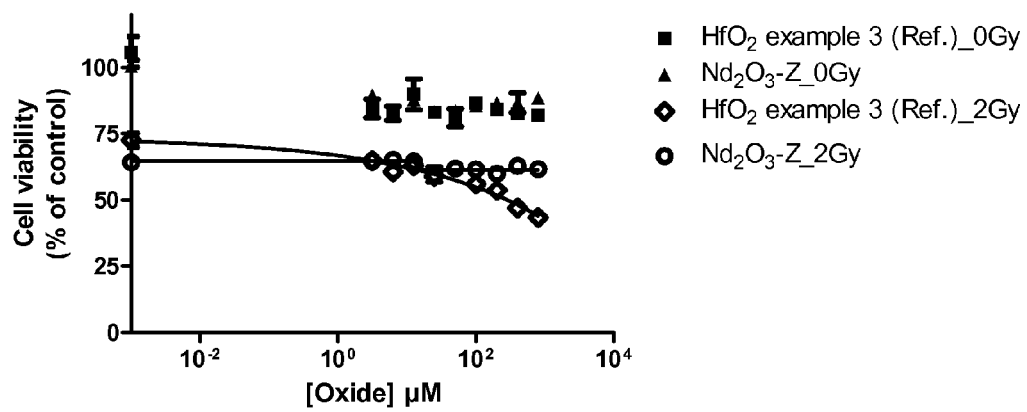

With nanoparticles ($HfO_2$-Ref./example 3/d=8.3) and without irradiation: filled square dots With nanoparticles ($HfO_2$-Ref./example 3/d=8.3) and with irradiation: open losange dots With nanoparticles ($CeO_2$-D d=6.6) and without irradiation: filled triangle dots With nanoparticles ($CeO_2$-D d=6.6) and with irradiation: open circle dots FIG. 12J shows the cell viability (% of control) after a 2 Gy irradiation using $Nd_2O_3$ nanoparticles or nanoparticle aggregates (400 µM) with density of 5.4 g/cm³ (example 10e)).

Figure 12K:
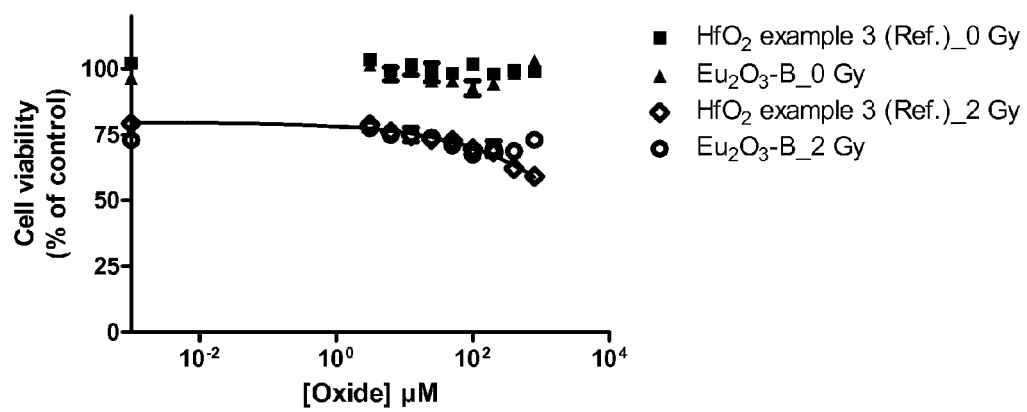

With nanoparticles ($HfO_2$-Ref./example 3/d=8.3) and without irradiation: filled square dots With nanoparticles ($HfO_2$-Ref./example 3/d=8.3) and with irradiation: open losange dots With nanoparticles ($Nd_2O_3$-Z d=5.4) and without irradiation: filled triangle dots With nanoparticles ($Nd_2O_3$-Z d=5.4) and with irradiation: open circle dots FIG. 12K shows the cell viability (% of control) after a 2 Gy irradiation using $Eu_2O_3$ nanoparticles or nanoparticle aggregates (400 µM) with density of 5.6 g/cm³ (example 10e)).

Figure 12L:
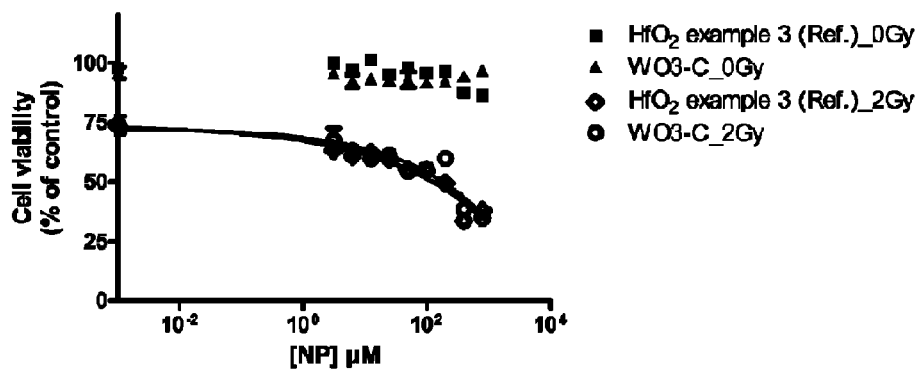

With nanoparticles ($HfO_2$-Ref./example 3/d=8.3) and without irradiation: filled square dots With nanoparticles ($HfO_2$-Ref./example 3/d=8.3) and with irradiation: open losange dots With nanoparticles ($Eu_2O_3$-B d=5.6) and without irradiation: filled triangle dots With nanoparticles ($Eu_2O_3$-B d=5.6) and with irradiation: open circle dots FIG. 12L shows the cell viability (% of control) after a 2 Gy irradiation using $WO_3$ nanoparticles or nanoparticle aggregates (400 µM) with density of 7.2 g/cm³ (example 10e)).

Figure 13:
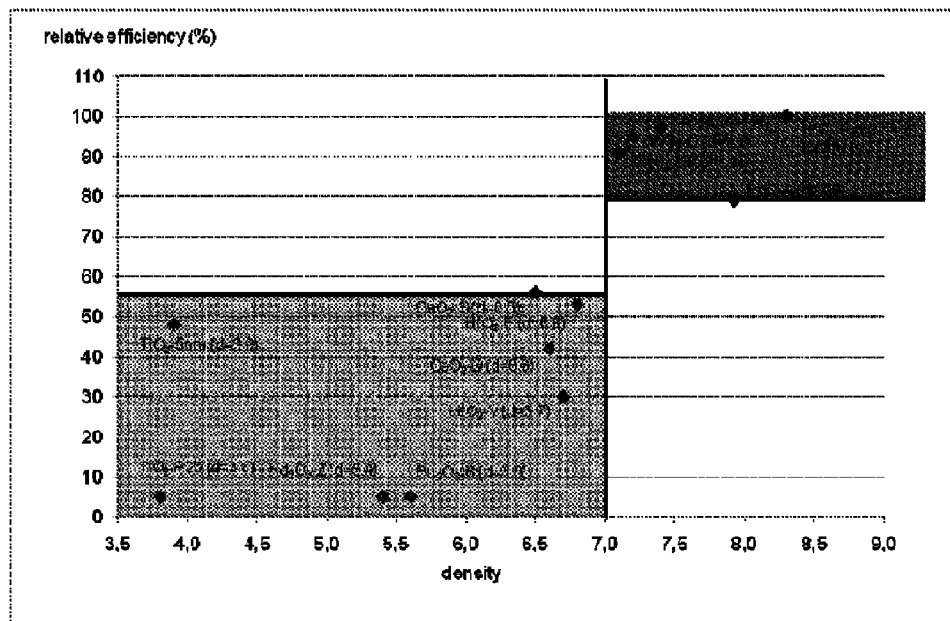

With nanoparticles (HfO$_2$-Ref./example 3/d=8.3) and without irradiation: filled square dots With nanoparticles (HfO$_2$-Ref./example 3/d=8.3) and with irradiation: open losange dots With nanoparticles (WO$_3$-C d=7.2) and without irradiation: filled triangle dots With nanoparticles (WO$_3$-C d=7.2) and with irradiation: open circle dots FIG. 13 presents the relative efficiency (ability to induce cell death), expressed as a percentage. Said relative efficiency reflects the cell viability (% of control), after a 2 Gy irradiation of the particles tested in example 10, at 800 μM, when compared to radiotherapeutic treatment alone (without nanoparticles), relatively to the cell viability (% of control) of biocompatible HfO$_2$ nanoparticles or nanoparticle aggregates (cf. example 3), at 800 μM, when compared to radiotherapeutic treatment alone (without nanoparticles).

Two groups of nanoparticles with significant differences in term of efficiency are distinguished:
- density<7 g/cm$^3$: the relative efficiency of the tested nanoparticles is below about 55%
- density 7 g/cm$^3$: the relative efficiency of the tested nanoparticles is superior to about 80%.

Figure 14:
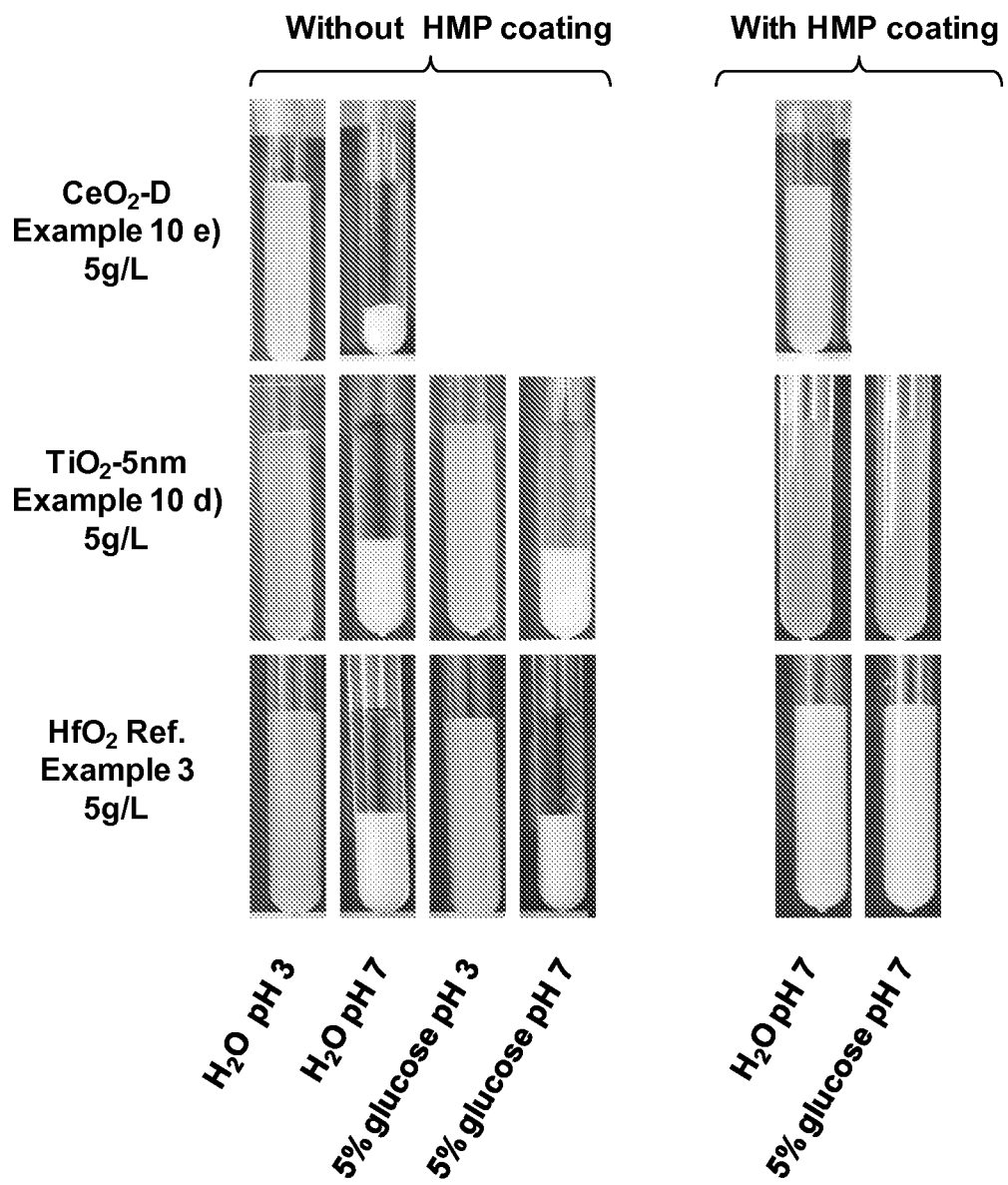

FIG. 14 reveals the stability or lack of stability of nanoparticles (cf. CeO$_2$-D of example 10e), TiO$_2$-5 nm of example 10d) and HfO$_2$ of example 3) at concentration about 5 g/L comprising or not a HMP biocompatible coating, in different conditions: samples were incubated 2 hours in water or in a 5% glucose solution at pH3 or pH 7 (cf. example 11).

FIG. 15 shows results of 0.22 μm filtration tests (cf. example 11): the different samples (CeO$_2$-D of example 10e), TiO$_2$-5 nm of example 10d) and HfO$_2$ of example 3) contain, or not, a HMP biocompatible coating (incubated 2 hours in water or in a 5% glucose solution, at pH 7). Concentrations are expressed in g/L, and filtration yield in %.

DETAILED DESCRIPTION OF THE INVENTION

It has been surprisingly found by inventors that a nanoparticle made of an inorganic material comprising oxygen, preferably a crystallized inorganic material comprising oxygen, even more preferably an oxide, the density of said inorganic material being of at least 7 g/cm$^3$, preferably above 7 g/cm$^3$, in particular, for a nanoparticle made of an oxide, above 7 g/cm$^3$ and below 15 g/cm$^3$, can enhance the therapeutic effect of a local irradiation intended to disturb, alter or destroy abnormal cells, tissues or organs in an animal.

A strong enhancement of radiotherapy efficacy in vitro can be observed for the first time using nanoparticles according to the present invention (cf. FIGS. 5B, 8, 10, 11A and 11B for example).

Inventors herein provide the proof that tumors in animals are reduced in size and eventually disappear (complete remission) after the injection of the herein described nanoparticles when said animals are locally exposed to a low dose irradiation able to activate said nanoparticles (see experimental part and FIGS. 6, 7 and 9).

In the spirit of the invention, the term "nanoparticle" or "nanoparticle aggregate" refers to synthetic products of small size. Their shape can be for example round, flat, elongated, spherical or oval, and the like. The shape can be determined or controlled by the method of production, and adapted by the person of the art according to the desired applications.

The shape of the particles does not have a major influence on their properties. However, the shape can influence the "biocompatibility" of the particles. Thus, for pharmacokinetic reasons, nanoparticles or nanoparticle aggregates being essentially elongated, spherical or round in shape are preferred. Spherical or round shape is particularly preferred. Also, particles or nanoparticle aggregates having a quite homogeneous shape are preferred.

In a preferred manner, the size of the particles or nanoparticle aggregates according to the invention is typically comprised between around 3 nm and 400 nm, preferably between around 5, 10, 15 or 20 nm and 200 nm, even more preferably between around 20 and 100 nm or around 40 nm and 100 nm.

In fact, the size of the objects must ideally be small enough to enable them to diffuse in the body (tissues, cells, blood vessels, etc.), essentially without being captured by macrophages (phagocytosis) and without causing significant obstruction.

Advantageously, such effects can be obtained in humans with particles having a mean particle size below 100 nm.

The aggregation may lead to the fusion of individual nanoparticles within the aggregate structure.

Nanoparticles having a low specific surface area are preferred in order to limit their interactions with the surrounding environment. For the purpose of the present invention, the nanoparticle specific surface area is for example comprised between about 10 m$^2$/g and 80 m$^2$/g. The specific surface area is preferentially comprised between 20 and 60 m$^2$/g.

The surprising efficiency of the nanoparticles according to the present invention is mainly due to the nature of their constitutive material which is an inorganic material comprising oxygen, preferably a crystallized material, the density of which is of at least 7 g/cm$^3$, preferably above 7 g/cm$^3$, in particular, for a nanoparticle made of an oxide, above 7 g/cm$^3$ and below 15 g/cm$^3$, in particular between 8 and 14 g/cm$^3$, or 8 and 12 g/cm$^3$. Such a nanoparticle is indeed capable of absorbing ionizing radiations and of emitting a sufficient amount of electrons and/or high energy photons, in particular when using low ionizing radiations, for them to be directly responsible for the alteration or destruction of a target cell, tissue or organ. It is to note that the present invention is also advantageously usable under high ionizing radiation (cf. FIG. 11B).

Doses of ionizing radiations are preferably doses comprised between around 0.05 Gray and 6 Grays for applications performed in vitro.

Doses are comprised between more than 0.05 Gray and less than 16 or 30 Grays for applications performed, in particular locally, ex vivo or in vivo. Total ionizing radiations range from 1.5 Gray up to around 85 Grays in the human according to the current practice.

The total dose of radiations delivered can be given following different schedules such as single dose, fractionated doses, hyperfractionated doses, etc.

Irradiated nanoparticles herein described provide, as demonstrated in the experimental section, a clear therapeutic effect improvement when compared to standard radiotherapy.

The above mentioned inorganic material is preferably an inorganic material. In a preferred embodiment of the present invention, the inorganic material is an oxide.

An oxide is a chemical compound containing at least one oxygen atom and at least a second distinct chemical element. Said distinct chemical element can be used as a precursor in the herein described methods for preparing a nanoparticle or nanoparticle aggregate. In the context of the present invention, a preferred oxide is a metal oxide (MA) (see "*Metal Oxide Chemistry and Synthesis—from solution to solid state*", Jean-Pierre Jolivet, Savoirs Actuels InterEditions/CNRS, Editions 1994) and a tungstate ($M_x(WO_4)_y$).

Metal oxide usable in the context of the present invention may be selected from the group consisting of an oxide from a lanthanide element and an oxide from a chemical (metallic) element of the periodic classification of elements (Mendeleev's table), in particular an oxide from a metallic element of periods 5 and 6 of the periodic classification.

In the context of the present invention, examples of elements that can be used are indicated below:

appropriate oxides from a lanthanide element may be selected for example from the group consisting of $CeO_2$, $Nd_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Lu_2O_3$ and mixtures thereof;

appropriate oxides from a metallic element of period 6 of the periodic classification of elements may be selected for example from the group consisting of $HfO_2$, $TaO_2$, $Ta_2O_5$, $WO_2$, $WO_3$, $ReO_2$, $OsO_2$, $IrO_2$, $PtO$, $PtO_2$, $HgO$, $Hg_2O$, $Tl_2O_3$, $PbO$, $Pb_2O_3$, $Pb_3O_4$, $PbO_2$, $PoO_2$, $Bi_2O_3$ and mixtures thereof;

appropriate oxides from a metallic element of period 5 of the periodic classification of elements may be selected for example from the group consisting of $NbO$, $RuO_2$, $Rh_2O_3$, $RhO_2$, $PdO$, $Ag_2O$, $AgO$, $CdO$, $In_2O_3$, and mixtures thereof.

Tungstate ($M_x(WO_4)_y$) can further be used as an inorganic material comprising oxygen, in the context of the present invention.

Preferred tungstates may be selected from the group consisting of for example $FeWO_4$, $CuWO_4$, $MnWO_4$, $PbWO_4$ and mixtures thereof.

Mixture of oxide(s) and tungstate(s) in a particular nanoparticle is also possible.

As indicated previously, nanoparticles according to the present invention have to be made of an inorganic material comprising oxygen, the density of said inorganic material being of at least 7 g/cm³, preferably above 7 g/cm³, in particular, for a nanoparticle made of an oxide, above 7 g/cm³ and below 15 g/cm³, in particular between 8 and 14 g/cm³, or 8 and 12 g/cm³.

Density is mass m per unit volume V. In the context of the present invention, improved therapeutic efficacy is obtained using nanoparticles having a high density. The density threshold required to get such improved therapeutic efficacy has been herein identified by inventors as 7 g/cm³. It is to be understood that the highest densities are preferred. Particularly preferred densities are of at least 7.5 g/cm³, preferably at least 8 g/cm³, even more preferably of at least 8.5, 9, 9.5, 10, 10.5, 11, 11.5, 12, 12.5, 13, 13.5 or 14 g/cm³.

Density of the nanoparticles or nanoparticles aggregates is determined from approximately 1 g of dried powder using Accupyc 1340 picnometer equipment.

The nanoparticles herein described are preferably made of an inorganic material having an effective atomic number ($Z_{eff}$) of at least 50, preferably at least 60 or 61, more preferably at least 65, 66, 67 or even 68.

Effective atomic number is a term that is similar to atomic number but is used for compounds (e.g. water) and mixtures of different materials (such as tissue and bone) rather than for atoms. Effective atomic number calculates the average atomic number for a compound or mixture of materials. It is abbreviated $Z_{eff}$.

The effective atomic number is calculated by taking the fractional proportion of each atom in the compound and multiplying that by the atomic number of the atom. The formula for the effective atomic number, $Z_{eff}$, is as follows:

$$Z_{eff} = \sqrt[2.94]{f_1 \times (Z_1)^{2.94} + f_2 \times (Z_2)^{2.94} + f_3 \times (Z_3)^{2.94} + \ldots}$$

where $f_n$ is the fraction of the total number of electrons associated with each element, and $Z_n$ is the atomic number of each element.

The atomic number (also known as the proton number) is the number of protons found in the nucleus of an atom. It is traditionally represented by the symbol Z. The atomic number uniquely identifies a chemical element. In an atom of neutral charge, atomic number is equal to the number of electrons.

An example is that of water ($H_2O$) which is made up of two hydrogen atoms (Z=1) and one oxygen atom (Z=8). The total number of electrons is 1+1+8=10. The fraction of electrons corresponding to the two hydrogens is 2/10 and the fraction of electrons corresponding to the unique oxygen is (8/10). $Z_{eff}$ of water is therefore:

$$Z_{eff} = \sqrt[2.94]{0.2 \times 1^{2.94} + 0.8 \times 8^{2.94}} = 7.42$$

$Z_{eff}$ participate to the incoming radiations absorption capacity of nanoparticles.

The following Table 1 provides examples of compounds, usable in the context of the present invention, and identifies their respective density and $Z_{eff}$.

TABLE 1

|  | Formula | $Z_{eff}$ | density (g/cm³) |
|---|---|---|---|
| Oxide |  |  |  |
| Cerium (IV) oxide | $CeO_2$ | 53.40 | 7.2 |
| Neodynium (III) oxide | $Nd_2O_3$ | 56.40 | 7.2 |
| Samarium (III) oxide | $Sm_2O_3$ | 58.39 | 7.6 |
| Europium (III) oxide | $Eu2O_3$ | 59.38 | 7.4 |
| Gadolinium (III) oxide | $Gd_2O_3$ | 60.37 | 7.4 |
| Terbium (III) oxide | $Tb_2O_3$ | 61.37 | 7.9 |
| Dysprosium (III) oxide | $Dy_2O_3$ | 62.36 | 7.8 |
| Holmium oxide | $Ho_2O_3$ | 63.36 | 8.4 |
| Erbium oxide | $Er_2O_3$ | 64.35 | 8.6 |
| Thullium (III) oxide | $Tm_2O_3$ | 65.34 | 8.6 |
| Ytterbium oxide | $Yb_2O_3$ | 66.34 | 9.2 |
| Lutetium oxide | $lu_2O_3$ | 67.33 | 9.4 |
| Hafnium (IV) oxide | $HfO_2$ | 67.26 | 9.7 |
| Tantalum (IV) oxide | $TaO_2$ | 68.25 | 10.0 |
| Tantalum (V) oxide | $Ta_2O_5$ | 67.24 | 8.2 |
| Tungsten(IV) oxide | $WO_2$ | 69.24 | 10.8 |
| Tugnsten (VI) oxide | $WO_3$ | 67.27 | 7.2 |
| Rhenium (IV) oxide | $ReO_2$ | 70.23 | 11.4 |
| Osmium (IV) oxide | $OsO_2$ | 71.23 | 11.4 |
| Iridium (IV) oxide | $IrO_2$ | 72.22 | 11.7 |
| Platinum (II) oxide | $PtO$ | 75.46 | 14.1 |
| Platinum (IV) oxide | $PtO_2$ | 73.21 | 11.8 |
| Mercury (I) oxide | $Hg_2O$ | 78.68 | 9.8 |
| Mercury (II) oxide | $HgO$ | 77.45 | 11.1 |
| Thallium (III) oxide | $Tl_2O_3$ | 77.29 | 10.2 |
| Lead (II) oxide (massicot) | $PbO$ | 79.45 | 9.6 |
| Lead (IV) oxide | $PbO_2$ | 77.18 | 9.6 |
| Lead (II,IV) oxide | $Pb_2O_3$ | 78.28 | 10.1 |
| Lead (II,II,IV) oxide | $Pb_3O_4$ | 78.66 | 8.9 |
| Polonium (IV) oxide | $PoO_2$ | 79.17 | 8.9 |
| Bismuth oxide | $Bi_2O_3$ | 79.28 | 8.9 |
| Niobium (II) oxide | $NbO$ | 38.61 | 7.3 |
| Ruthenium (IV) oxide | $RuO_2$ | 39.63 | 7.1 |
| Rhodium (III) oxide | $Rh_2O_3$ | 41.55 | 8.2 |
| Rhodium (IV) oxide | $RhO_2$ | 40.61 | 7.2 |

TABLE 1-continued

|  | Formula | $Z_{eff}$ | density (g/cm³) |
|---|---|---|---|
| Palladium (II) oxide | PdO | 43.57 | 8.3 |
| Silver(I) oxide | Ag$_2$O | 45.72 | 7.2 |
| Silver(II) oxide | AgO | 44.57 | 7.5 |
| Cadmium oxide | CdO | 45.56 | 8.2 |
| Indium oxide | In$_2$O$_3$ | 45.50 | 7.2 |
| Tungstate |  |  |  |
| Iron tungstate | FeWO$_4$ | 61.1 | 7.5 |
| Copper tungstate | CuWO$_4$ | 60.8 | 7.5 |
| Lead tungstate | PbWO$_4$ | 73.6 | 8.5 |

The highest the nanoparticle or nanoparticle aggregate density and $Z_{eff}$, the more efficient is the absorption of ionizing radiations. The electrons and/or high energy photons emission is then amplified following irradiation thereby enhancing the therapeutic efficacy.

Inventors herein surprisingly highlight the fundamental and direct role of the density parameter on the photons and electrons emission amplification, said amplification allowing therapeutic applications in a mammal, as herein explained, when the density reaches, and preferably exceeds, the 7 g/cm³ threshold (see experimental part). Examples 4, 10a) and 10b) regarding HfO$_2$ and CeO$_2$ nanoparticles, further provide results highlighting the surprising influence of density for a constant $Z_{eff}$.

The nanoparticles or aggregates according to the present invention are advantageously biocompatible, that is to say, they can be safely administered to an animal organism, typically a mammal, in particular a human, to provide their therapeutic effect. Said biocompatibility can be ensured for example by the nature of the compound(s) or material(s) constituting the particle and/or by an optional coating.

Preferred nanoparticles or aggregates according to the invention are covered with a biocompatible coating. When the nanoparticles and/or aggregates of the present invention are administered to a subject via the intravenous (IV) route, such a biocompatible coating is particularly advantageous to optimize the biodistribution of nanoparticles and aggregates in the context of the previously described EPR effect. A full biocompatible coating of the nanoparticle or aggregate is required, in particular in the IV context, in order to avoid interaction of the particle surface with any recognition element (macrophage, opsonins, etc.). The "full coating" implies the presence of a very high density of biocompatible molecules able to create at least a complete monolayer on the surface of the particle. Said coating is responsible for the so called "stealth effect" of the nanoparticle or aggregate.

The biocompatible coating allows in particular the nanoparticle stability between pH 6.5 and 7.5 in a biocompatible suspension, such as a physiological fluid (blood, plasma, serum, etc.), any isotonic media or physiologic medium, for example media comprising glucose (5%) and/or NaCl (0.9%) (cf. example 11 and FIG. 14), which is required for a pharmaceutical administration.

Such a biocompatible coating is obtained by treating the nanoparticle with a surface treating agent.

Stability may be confirmed by dry extract quantification measured on a nanoparticle suspension prior and after filtration on a 0.22 µm filter (cf. example 11 and FIG. 15). Advantageously, said coating preserves the integrity of the particles in vivo, ensures or improves the biocompatibility thereof, and facilitates an optional functionalization thereof (for example with spacer molecules, biocompatible polymers, targeting agents, proteins, etc.). A particular nanoparticle according to the present invention indeed further comprises a targeting agent to allow its interaction with a recognition element present on the target cell. Such targeting agents will act once the nanoparticles or aggregates are accumulated in the tumor. As the conformation of the targeting agent will be responsible for its interaction with the target, the density of said targeting agent is to be controlled carefully. A high density thereof can indeed perturb the targeting agent conformation and in consequence its recognition by the target ("*Folate-targeted, cationic liposome-mediated gene transfer into disseminated peritoneal tumors.*"; J A Reddy, C Abburi, H Hofland, S J Howard, I Vlahov, P Wils & C P Leamon; Gene therapy (2002) 9 p 1542-1550/ "*Folate targeting of drug carriers: A mathematical model.*"; Ketan B. Ghaghadaa, b, Justin Sauld, e, ayaganesh V. Natarajanb, c, Ravi V. Bellamkondad, e, Ananth V. Annapragadaa, b, T.; Journal of Controlled Release 104 (2005) 113-128). In addition, a high target agent density may favour nanoparticles clearance by the Reticulo Endothelial System (RES) during circulation in the vasculature.

The biocompatible coating can be composed of any amorphous or crystalline structure. It is preferable that the coating allows the diffusion of small molecules and free radicals. In particular, it is important that the coating allows the passage of water (or O$_2$) and preferably the passage of the radical form thereof (the biocompatible coating will not dissolve between pH 6.5 and 7.5). This can be accomplished by using materials which are porous and/or by adding a coating layer having a low thickness and being porous. Thus, a typical porosity of the coating is comprised between around 0.05 and 10 nm, preferably 0.1, or 0.2 and 5 nm. A typical coating thickness is generally comprised between around 0.2 and 50 nm, for example between around 0.5 and 5 nm or around 10 and 40 nm.

In general, the coating can be non-biodegradable or biodegradable. Both options can be used for the purpose of this invention.

Examples of non-biodegradable coatings are one or more materials or surface treating agents selected in the group consisting of silica, alumina, sugar (agarose for example), phosphate, silane, switterionic compounds, lipids, saturated carbon polymers (polyethylene oxide for example) and inorganic polymers, reticulated or not, modified or not (polymethacrylate or polystyrene for example), as well as combinations thereof.

Examples of biodegradable coatings are for example one or more materials or surface treating agents selected from the group consisting of a biological molecule, modified or not, natural or not and a biological molecular polymer; modified or not, of natural shape or not. The biological polymer may be a phospholipid, a saccharide, an oligosaccharide or a polysaccharide, polysulfated or not, for example dextran.

The aforementioned materials, compounds or surface treating agents can be used alone or in combinations, mixtures or assemblies, composite or not, covalent or not, optionally in combination with other compounds. Moreover, it is also possible to use any one of the aforementioned material, said material being naturally water-soluble or lipid-soluble or being artificially modified to become water-soluble or lipid-soluble.

The biocompatible coating preferably comprises or is made of a compound selected in the group consisting of an inorganic agent, a metallic agent, an organic agent, and a mixture or combination thereof.

Appropriate inorganic agent may be selected from the group consisting of an oxide, an hydroxide, and an oxyhydroxide. The inorganic agent may comprise for example silicium, aluminium, zirconium, calcium, magnesium and/or tin.

Such agents can be used to charge the nanoparticle either positively or negatively in order to modulate interactions of said nanoparticle with the biological media.

An inorganic agent selected from the group consisting of for example magnesium and calcium will bring a positive charge to the surface of the nanoparticle at a pH of 7.

For example, the silicium may be used to bring a negative charge to the surface of the nanoparticle at a pH of 7.

Appropriate metallic agent may be selected from the group consisting of gold, silver and platinum.

An appropriate organic agent may be any agent comprising a function capable of interacting with a nanoparticle according to the present invention and a function conferring biocompatibility to said nanoparticle.

The agent comprising a function capable of interacting with a nanoparticle may be for example a carboxylate ($R-COO^-$), a sulfate ($R-SO_4^{2-}$), an alcohol ($R-OH$), a silane ($R-Si(OR)_3$), an amine ($R-NH_2$), a quaternary ammonium ($R-NH_4^+$), a phosphonic function ($R-PO(OH)_2$) or a phosphoric function ($R-O-PO(OH)_2$).

The agent comprising a function capable of conferring biocompatibility to a nanoparticle according to the present invention may have a steric function and/or an electrostatic function. Such agent with a steric function may be selected from the group consisting of polyethylene glycol (PEG), polyethylenoxide, Polyvinylalcohol, Polyacrylate, Polyacrylamide (poly(N-isopropylacrylamide)), Polycarbamide, a biopolymer or polysaccharide such as Dextran, Xylan, cellulose, collagene, and a switterionic compound such as polysulfobetain, etc.

Agent with a positive electrostatic function may be an amine such as aminopropyltriethoxisilane, or polylysine.

Agent with a negative electrostatic function may be selected from the group consisting of phosphate (for example a polyphosphate, a metaphosphate, a pyrophosphate, etc.), carboxylate (for example citrate or dicarboxylic acid, in particular succinic acid) and sulphate.

The coating can also contain different functional groups (or linker segments), allowing any molecule of interest to bind to the surface of the particle.

A typical example of a nanoparticle according to the invention is a nanoparticle made of $HfO_2$ comprising a phosphate compound such as sodium trimetaphosphate (STMP) or sodium hexametaphosphate (HMP) as a biocompatible coating.

Another example of a nanoparticle according to the invention is a nanoparticle made of $HfO_2$ comprising, as a biocompatible coating, a silane bearing at least one functional group selected from the group consisting of a metallic agent, polyethylene, an oxide, an amine, an anhydride, a phosphate and any combination thereof.

Another object of the invention relates to a method of producing a nanoparticle or nanoparticle aggregate such as defined hereinabove or a mixture thereof, comprising:

providing a chemical element allowing the preparation of an inorganic material comprising oxygen, the density of said material being of at least 7 g/cm³, preferably above 7 g/cm³, in particular, for a nanoparticle made of an oxide, above 7 g/cm³ and below 15 g/cm³, preparing a nanoparticle or nanoparticle aggregate from said chemical element by precipitation of said chemical element in a polar medium (such as an aqueous solution, an alcohol solution, etc.) and by crystallisation, and, optionally coating the nanoparticle or aggregate using a surface treating agent as described previously.

During the precipitation step:

pH is preferably advantageously adjusted between around 7 and 14;

the precursor (chemical element) concentration is preferably advantageously adjusted between around $10^{-3}$ and 3 mol/l;

ionic strength is preferably advantageously adjusted between around $10^{-3}$ mol/l and 5 mol/l; preferably between around $10^{-3}$ mol/l and 3 mol/l;

temperature is preferably advantageously adjusted between around 20° C. and 350° C.

Before being optionally coated, the inorganic material is preferably crystallized for example via thermal treatment (such a treatment may be followed by a wet or dry milling step). Precipitation and crystallisation steps may be performed simultaneously or sequentially.

A sequestering (complexing) agent can further be added to the polar medium to help reaching the desired crystallisation phase, crystallinity, particle shape, particle size and/or density.

The crystallized material may also be washed (to remove any impurity) and/or peptized (in order to bring an electrical charge on the surface of the inorganic particle in order to confer stability to said nanoparticle at a given pH).

The coating step advantageously consists in placing the nanoparticle or nanoparticle aggregate in contact with a surface treating agent (also herein called "coating") as defined previously.

In a particular embodiment, a method of producing a suspension of biocompatible nanoparticles, nanoparticle aggregates or a mixture thereof comprises the following steps, preferably in order:

a) providing as a precursor, a chemical element from the group of lanthanide, or of period 5 or 6 of the periodic classification, which is able to form an inorganic material comprising oxygene, in particular an oxide or a tungstate, preferably an oxide, the density of said material being of at least 7 g/cm³, preferably above 7 g/cm³, in particular, for a nanoparticle made of an oxide, above 7 g/cm³ and below 15 g/cm³, in particular between 8 and 14 g/cm³, or 8 and 12 g/cm³, b) precipitating the precursor of step a) in a polar medium by preferably adjusting the pH, temperature, ionic strength of the medium and/or precursor concentration, and optionally adding a complexing agent, c) optionally crystallizing the precipitate via thermal treatment, d) optionally washing the suspension obtained at the end of step b) or c) to remove any impurities, salt and/or complexing agent present therein, e) optionally performing a peptization step in order to bring a charge to the surface of the nanoparticles or aggregates present in the suspension, and optionally f) coating the nanoparticles or aggregates.

The pH of the suspension of nanoparticle or nanoparticle aggregates obtained with a method as previously described may be adjusted with physiological medium (between pH 6.5 and 7.5).

The suspensions described above may be further submitted to a formulation step before being administered to a subject.

In a particular example, a method of producing a nanoparticle or nanoparticle aggregate, the nanoparticle being made of, or comprising a core made of, $HfO_2$, preferably comprises the following steps in order:

precipitating a solution of Hafnium precursor (such as in particular $HfCl_4$ or $HfOCl_2$ solution) with a base, such as in particular tetramethylammonium hydroxide (TMAOH), crystallizing the amorphous inorganic suspension thus obtained, for example via thermal treatment above 50° C., preferably at least 100° C., while optionally stirring the suspension, optionally washing and/or peptizing the crystallized material thus obtained, optionally coating said crystallized material by placing said material in contact with a surface treating agent as defined previously.

Another object of the invention is based on any composition comprising nanoparticles or aggregates such as defined hereinabove and/or which can be obtained by the methods herein described. While not mandatory, the particles in the inventive compositions advantageously have quite homogeneous size and shape.

A particular object of the invention relates to a pharmaceutical composition comprising particles or nanoparticle aggregates such as defined hereinabove and, optionally, a pharmaceutically acceptable excipient or vehicle.

Another particular object of the invention relates to a diagnostic or imaging composition comprising particles or nanoparticle aggregates such as defined hereinabove and, optionally, a physiologically acceptable excipient or vehicle.

The compositions can be in the form of a solid, liquid (particles in suspension), aerosol, gel, paste, and the like. Preferred compositions are in liquid form.

The excipient or vehicle which is employed can be any classical support for this type of application, such as for example saline, isotonic, sterile, buffered solutions, and the like. They can also comprise stabilizers, sweeteners, surfactants, and the like. They can be formulated for example as ampoules, aerosol, bottles, tablets, capsules, by using known techniques of pharmaceutical formulation.

In the herein described compositions, appropriate or desirable concentrations of nanoparticles are comprised between around $10^{-3}$ mg of nanoparticles/gram of tumor and around 100 mg of nanoparticles/gram of tumor, in particular between around 5 and 50 mg of nanoparticles/gram of tumor. This includes different routes of administration.

Generally, the compositions in liquid form comprise between 0.05 g/L and 300 g/L of nanoparticles, 0.05 g/L and 150 g/L, preferably at least 10 g/L, 20 g/L, 40 g/L, 45 g/L, 50 g/L, 55 g/L, 60 g/L, 80 g/L, 100 g/L, 150 g/L, 200 g/L or 250 g/L.

Dry extract is ideally measured following a drying step of the suspension comprising the nanoparticles.

The compositions, particles and aggregates of the invention can be used in many fields, particularly in human or veterinary medicine.

It is an object of the present invention to use a nanoparticle or nanoparticle aggregate as herein described to alter, destroy or eliminate a target cell, tissue or organ.

Under the effect of ionizing radiations, X-Rays, gamma-rays, radioactive isotopes and/or electron beams in particular, the nanoparticles are excited and produce electrons and/or high energy photons.

Said electrons and/or high energy photon, upon contact with surrounding media, water or $O_2$ in particular, can generate free radicals and or new ionizations.

Depending on the energy of ionizing radiations, the particles can thus enable the destruction of tissues and/or, simply, a visualization for imaging and/or for diagnostics purposes.

Hence a particular object of the invention is based on the use of a nanoparticle or nanoparticle aggregate according to the present invention to prepare a pharmaceutical composition intended to alter, destroy or eliminate target cells in an animal, when said cells are exposed to radiations, in particular to ionizing radiations, and on the corresponding methods.

The pharmaceutical can further comprises an additional therapeutic compound, distinct from a nanoparticle or nanoparticle aggregate, also intended to treat cancer.

Another particular object of the invention is based on a method for inducing or causing the lysis, apoptosis or destruction of target cells, in vitro, ex vivo or in vivo, comprising contacting cells, in particular target cells, with one or more nanoparticles or nanoparticle aggregates such as defined hereinabove, during a period of time sufficient to allow the particles or aggregates to penetrate inside the target cells or to interact with said cells and, exposing the cells to radiations, appropriate radiations being in particular ionizing radiations, preferably X-Rays, γ-Rays, radioactive isotopes and/or electron beams, said exposure inducing or causing the lysis, apoptosis or destruction of said target cells.

The target cells can be any pathological cells, that is to say, cells involved in a pathological mechanism, for example proliferative cells, such as tumor cells, stenosing cells (fibroblast/smooth muscle cells), or immune system cells (pathological cell clones). A preferred application is based on the treatment (for example the destruction or functional alteration) of malignant cells or tissue.

In this regard, a particular object of the invention is based on the use of compositions, particles or nanoparticle aggregates such as defined hereinabove (in combination with ionizing radiations as defined previously) for producing a pharmaceutical composition intended for the treatment of cancer.

The present disclosure further encompasses the use of compositions, particles or nanoparticle aggregates such as defined hereinabove to prevent or treat a cancer or to alleviate the symptoms of a cancer in an animal, when said cells are exposed to radiations, in particular to ionizing radiations as defined previously.

Another particular object of the invention is based on a method for inducing or causing the lysis or destruction of cancer cells, in vitro, ex vivo or in vivo, comprising contacting cancer cells with one or more particles or nanoparticle aggregates such as defined hereinabove, during a period of time sufficient to allow the particles or aggregates to penetrate inside the cancer cells or to interact with said cells and, exposing the cells to radiations, in particular to ionizing radiations as defined previously, said exposure inducing or causing the lysis or destruction of said cells.

Another object of the invention relates to a method for preventing or treating a cancer or alleviating the symptoms of a cancer in a subject or patient, comprising administering to the patient suffering from a cancer a composition, nanoparticles or nanoparticle aggregates such as defined hereinabove, in conditions allowing the particles or nanoparticle aggregates to penetrate inside the abnormal cells or to interact with said cells, in particular cancer cells, and subsequently treating the subject in the presence of a source of excitation, in particular a source of ionizing radiations, leading to an alteration, disturbance or functional destruction of the patient's abnormal cells, thereby preventing or treating a cancer.

Classical cancer management systematically implies the concurrence of multimodality treatments (combination of radiotherapy and chemotherapy for example).

The herein described nanoparticles submitted to ionizing radiations, in the context of radiotherapy, can be used in association with a different cancer therapy protocol. Such a protocol can be selected from the group consisting of surgery, radiosurgery, chemotherapy, a treatment comprising administration of cytostatic(s), cytotoxic(s), a targeted therapy, a vaccine, radionuclides, in particular immunoradionuclides, and any other biological or inorganic product intended to treat cancer.

Surprisingly, the herein described nanoparticles can further be used in the context of radiotherapy alone with increased observed efficacy.

The invention can be used to treat any type of malignant tumor such as haematological tumors or malignancies, and solid tumors, in particular of epithelial, neuroectodermal or mesenchymal origin. In addition, nanoparticles can be used to treat a premalignant lesion or a specific benign disease where radiation therapy is classically used and/or indicated.

The invention is applicable, in the context of therapy, to primary tumors, or secondary invasions, loco-regional or distant metastases, and in the context of prophylaxis, in order to avoid secondary malignant central nervous system involvement such as the observed invasions (metastasis) from melanoma, lung cancer, kidney cancer, breast cancer, etc.

The nanoparticles can be used at any time throughout the anticancer treatment period. They can be administered for example as a neoadjuvant (before surgical intervention for cancer exeresis) or as an adjuvant (after surgery).

The nanoparticles can also be used for advanced tumors which can not be surgically removed.

As herein explained, the irradiation can be applied at any time after administration of the particles, on one or more occasions, by using any currently available system of radiotherapy or radiography.

The nanoparticles herein described are in particular intended to be used to treat cancer where radiotherapy is a classical treatment. Such cancer may be selected in particular from the group consisting of skin cancer, including malignant neoplasms associated to AIDS, melanoma; central nervous system tumors including brain, stem brain, cerebellum, pituitary, spinal canal, eye and orbit; head and neck tumors; lung cancers; breast cancers; gastrointestinal tumors such as liver and hepatobiliary tract cancers, colon, rectum and anal cancers, stomach, pancreas, oesophagus cancer; male genitourinary tumors such as prostate, testis, penis and urethra cancers; gynecologic tumors such as uterine cervix, endometrium, ovary, fallopian tube, vagina and vulvar cancers; adrenal and retroperitoneal tumors; sarcomas of bone and soft tissue regardless the localization; lymphoma; myeloma; leukemia; and pediatric tumors such as Wilm's tumor, neuroblastoma, central nervous system tumors, Ewing's sarcoma, etc.

The particles can be excited within a large range of total dose of irradiation.

Amounts and schedules (planning and delivery of irradiations in a single dose, or in the context of a fractioned or hyperfractioned protocol, etc.) is defined for any disease/anatomical site/disease stage patient setting/patient age (children, adult, elderly patient), and constitutes the standard of care for any specific situation.

The irradiation can be applied at any time after administration of the particles, on one or more occasions, by using any currently available system of radiotherapy or radiography. The particles can be administered by different routes such as local (intra-tumoral (IT) in particular), subcutaneous, intra venous (IV), intra-dermic, intra-arterial, airways (inhalation), intra peritoneal, intra muscular and oral route (per os). The particles can further be administered in an intracavity such as the virtual cavity of tumor bed after tumorectomy.

Repeated injections or administrations can be performed, when appropriate.

The term "treatment" denotes any action performed to correct abnormal functions, to prevent diseases, to improve pathological signs, such as in particular a reduction in the size or growth of an abnormal tissue, in particular of a tumor, a control of said size or growth, a suppression or destruction of abnormal cells or tissues, a slowing of disease progression, a disease stabilization with delay of cancer progression, a reduction in the formation of metastases, a regression of a disease or a complete remission (in the context of cancer for example), etc.

As indicated previously, appropriate radiations or sources of excitation are preferably ionizing radiations and can advantageously be selected from the group consisting of X-Rays, gamma-Rays, electron beams, ion beams and radioactive isotopes or radioisotopes emissions. X-Rays is a particularly preferred source of excitation.

Ionizing radiations are typically of about 2 KeV to about 25 000 KeV, in particular of about 2 KeV to about 6000 KeV (LINAC source), or of about 2 KeV to about 1500 KeV (such as a cobalt 60 source).

In general and in a non-restrictive manner, the following X-Rays can be applied in different cases to excite the particles:

Superficial X-Rays of 2 to 50 keV: to excite nanoparticles near the surface (penetration of a few millimeters);
X-Rays of 50 to 150 keV: in diagnostic but also in therapy;
X-Rays (ortho voltage) of 200 to 500 keV which can penetrate a tissue thickness of 6 cm;
X-Rays (mega voltage) of 1000 keV to 25,000 keV. For example the excitation of nanoparticles for the treatment of prostate cancer can be carried out via five focused X-Rays with an energy of 15,000 keV.

Radioactive isotopes can alternatively be used as a ionizing radiation source (named as curietherapy or brachytherapy). In particular, Iodine $I^{125}$ (t ½=60.1 days), Palladium $Pd^{103}$ (t ½=17 days), Cesium $Cs^{137}$ and Iridium $Ir^{192}$ can advantageously be used.

Charged particles such as proton beams, ions beams such as carbon, in particular high energy ion beams, can also be used as a ionizing radiation source and/or neutron beams.

Electron beams may also be used as a ionizing radiation source with energy comprised between 4 MeV and 25 Mev.

Specific monochromatic irradiation source could be used for selectively generate X-rays radiation at an energy close to or corresponding to the desired X-ray absorption edge of the atoms of the oxide nanoparticle or nanoparticles aggregate.

Preferentially sources of ionizing radiations may be selected from Linear Accelerator (LINAC), Cobalt 60 and brachytherapy sources.

In the field of diagnostics, the inventive nanoparticles can be used as contrast agents, for detecting and/or visualizing any type of tissue. Thus, an object of the invention is the use of compositions, particles or nanoparticle aggregates such as defined hereinabove, in combination with radiations, using in particular radiography devices, for producing a composition intended for the detection or the visualization of cells, tissues or organs.

The term "in combination" indicates that the sought-after effect is obtained when the cells, tissues or organs of interest, having partially incorporated the nanoparticles of the invention, are excited by the defined source. However, it is not necessary for the particles and Rays to be administered simultaneously, nor according to the same protocol.

The present disclosure further provides kits comprising any one or more of the herein-described nanoparticles or compositions. Typically, the kit comprises at least one nanoparticle or nanoparticle aggregate according to the present invention. Generally, the kit also comprises one or more containers filled with one or more of the ingredients of the pharmaceutical compositions of the invention. Associated with such container(s), a labelling notice providing instructions for using the products can be provided for using the nanoparticles, nanoparticle aggregates or compositions according to the present methods.

Other aspects and advantages of the invention will become apparent in the following examples, which are given for purposes of illustration and not by way of limitation.

EXPERIMENTAL SECTION

Example 1

Biocompatible suspension of hafnium oxide ($HfO_2$) nanoparticles or nanoparticle aggregates with a density above 7 $g/cm^3$, using sodium trimetaphosphate as cating agent.

A Tetramethylammonium hydroxide (TMAOH) solution is added to 40 g of $HfCl_4$ solution. Addition of TMAOH solution is performed until the pH of the final suspension reaches a pH comprised between 7 and 13. A white precipitate is obtained.

The precipitate is further transferred in an autoclave and heated at a temperature comprised between 120° C. and 300° C. to perform crystallization. After cooling, the suspension is washed with de-ionized water.

A peptization step, is performed in order to get a stable suspension of nanoparticles or nanoparticle aggregates.

Suspension of Sodium trimetaphosphate is then added to the peptized solution (the amount of sodium trimetaphosphate added being below lethal dose (LD) 50/5) and the pH of the suspension is adjusted to a pH comprised between 6.5 and 7.5.

For in vitro experiments a sterilization step is performed at this stage using a 0.22 μm filter.

For in vivo experiments, a formulation step using glucose 5% can be performed before or after the sterilization step.

The following table presents the main characteristics of the suspension of biocompatible nanoparticles or nanoparticle aggregates thus obtained.

| Density | Morphology (See FIG. 2A) | Specific surface area (SS) in $m^2/g$ | Mean hydrodynamic diameter ($\Phi$) in nm |
|---|---|---|---|
| 8.5 | Spherical in shape | 20 < SS < 60 | 15 < $\Phi$ < 200 |

Example 2

Biocompatible suspension of hafnium oxide ($HfO_2$) nanoparticles or nanoparticle aggregates with a density below 7 $g/cm^3$, using sodium trimetaphosphate as coating agent.

A Tetramethylammonium hydroxide (TMAOH) solution is added to 40 g of $HfCl_4$ solution. Addition of TMAOH solution is performed until the pH of the final suspension reaches a pH comprised between 1 and 5. A white precipitate is obtained.

The precipitate is further transferred in an autoclave and heated at a temperature comprised between 120° C. and 300° C. to perform crystallization. After cooling, the suspension is washed with de-ionized water.

A peptization step, is performed in order to get a stable suspension of nanoparticles or nanoparticle aggregates.

Suspension of Sodium trimetaphosphate is then added to the peptized solution (the amount of sodium trimetaphosphate added being below LD50/5) and the pH of the suspension is adjusted to a pH comprised between 6.5 and 7.5.

For in vitro experiments a sterilization step is performed at this stage using a 0.22 μm filter.

For in vivo experiments, a formulation step using glucose 5% can be performed before or after the sterilization step.

The following table presents the main characteristics of the suspension of biocompatible nanoparticles or nanoparticle aggregates thus obtained.

| Density | Morphology | Specific surface area (SS) in $m^2/g$ | Mean hydrodynamic diameter ($\Phi$) in nm |
|---|---|---|---|
| 6.5 | Spherical in shape | 20 < SS < 60 | 15 < $\Phi$ < 200 |

Example 3

Biocompatible suspension of hafnium oxide ($HfO_2$) nanoparticles or nanoparticle aggregates with a density above 7 $g/cm^3$, using sodium hexametaphosphate as coating agent.

A Tetramethylammonium hydroxide (TMAOH) solution is added to 40 g of $HfCl_4$ solution. Addition of TMAOH solution is performed until the pH of the final suspension reaches a pH comprised between 7 and 13. A white precipitate is obtained.

The precipitate is further transferred in an autoclave and heated at a temperature comprised between 120° C. and 300° C. to perform crystallization. After cooling, the suspension is washed with de-ionized water.

A peptization step, is performed in order to get a stable suspension of nanoparticles or nanoparticle aggregates.

Suspension of Sodium hexametaphosphate is then added to the peptized solution (the amount of sodium hexametaphosphate added being below LD50/5) and the pH of the suspension is adjusted to a pH comprised between 6.5 and 7.5.

For in vitro experiments a sterilization step is performed at this stage using a 0.22 μm filter.

For in vivo experiments, a formulation step using glucose 5% can be performed before or after the sterilization step.

The following table presents the main characteristics of the suspension of biocompatible nanoparticles or nanoparticle aggregates thus obtained.

| Density | Morphology (See FIG. 2A) | Specific surface area (SS) in $m^2/g$ | Mean hydrodynamic diameter ($\Phi$) in nm |
|---|---|---|---|
| 8.3 | Spherical in shape | 20 < SS < 60 | 15 < $\Phi$ < 200 |

Example 4

Cell Survival Analysis or Surviving Fraction at x grays ($SF_x$) analysis using biocompatible suspension of $HfO_2$ nanoparticles or nanoparticle aggregates as prepared in example 1 and example 2 (FIG. 5B).

Materials and Method

Plating efficiency for each colon cancer cell line (radio sensitive HCT116 and radio resistant HT29 cancer cells) was determined before $SF_x$ determination. Cells were plated so that 50 to 200 colonies are formed per plate, and incubated between 3 hours and overnight at 37° C. to allow for adherence. Cells were then treated during a maximum incubation time of 24 h with 400 μM of $HfO_2$ nanoparticle or nanoparticles aggregate from both example 1 (with a density equal to 8.5) and example 2 (with density equal to 6.5).

Irradiation was performed using a 4 Gy irradiation for HT29 cancer cells and a 2 Gy irradiation for HCT116 cancer cells, with a 200 keV Irradiator (Tube Comet MXR-225/22-200 kV/15 mA/0.2 mm Cu). After irradiation, cells were incubated for more than 8 days at 37° C. before being stained with 0.5% crystal violet in absolute methanol. Only colonies with at least 50 cells were counted. $SF_x$ was determined by the following formula:

$$SF_x=[(\text{number of colonies}) \text{ at x dose}/(\text{total number of cells plated}) \text{ at x dose}] \times \text{plating efficiency}$$

Results: Effect of Density on Radiosensitive or Radioresistant Cells

As shown in FIG. 5B, irradiation had almost no significant effect on both the radio sensitive (HCT116) and radio resistant (HT29) cancer cells having incorporated, or being in contact with, $HfO_2$ nanoparticles or nanoparticle aggregates from example 2 (density equal to 6.5), compared to the untreated control cells. However, treatment of cancer cells with $HfO_2$ nanoparticles or nanoparticle aggregates from example 1 (density equal to 8.5), resulted in a significant increase in the level of radiation induced cell death in both radio sensitive (HCT116) and radio resistant (HT29) cancer cells.

Example 5

Clonogenic assay using biocompatible suspension of $HfO_2$ nanoparticles or nanoparticles aggregates from example 3 (FIG. 8):

Cell survival was quantified by standardized colony-forming assay. Glass culture dishes were transferred to the linear accelerator immediately after a maximum incubation time of 24 hours of cells with $HfO_2$ nanoparticles or nanoparticles aggregates (400 µM). Cells were irradiated with a different dose of irradiation (dose rate: 1 Gy/min, 200 keV: Tube Comet MXR-225/22-200 kV/15 mA/0.2 mm Cu, at room temperature).

Results on both radio sensitive and radio resistant cancer cells (FIG. 8) indicate the radiation enhancement ratio (ER) for the nanoparticles. HT29 cells showed an ER of 1.60 for the 4 Gy dose alone whereas HCT116 cells showed an ER of 1.33 for the equivalent dose. These data demonstrate that nanoparticles in combination with radiations are responsible for the clonogenic inhibition correlated with a decrease of cell survival in both radio-sensitive and radio-resistant cell lines.

Example 6

Cell viability assay using biocompatible suspension of $HfO_2$ nanoparticles or nanoparticles aggregates from example 3 (FIG. 10):

Cell viability was measured using the WST-1 kit after a 24 h-treatment period with or without nanoparticles (800 µM) with varying irradiation doses (up to 6 Gy) using a 200 KeV X-Rays irradiation (Tube Comet MXR-225/22-200 kV/15 mA/0.2 mm Cu). The effects of nanoparticles are presented on FIG. 10.

The presence of 800 µM nanoparticles leads to a decrease of cell viability when compared to a control deprived of any nanoparticles. Nanoparticles submitted to 1 Gy of X-Rays irradiation leads to a similar efficacy when compared to a control submitted to a 3 Gy X-Rays irradiation (radiotherapy alone).

No sign of toxicity was observed with nanoparticles alone. Experiments performed with 10 different concentrations showed consistent results.

This demonstrates clearly the dose enhancement effect of the nanoparticles. Surprisingly, efficient properties are observed at a low dose of radiotherapy: this indicates the possible use of nanoparticles using regular radiotherapy protocols but also offer the promise of a potential reduction of usual radiotherapy dose for a similar or better efficacy than usual treatment.

Example 7

Figure 1:
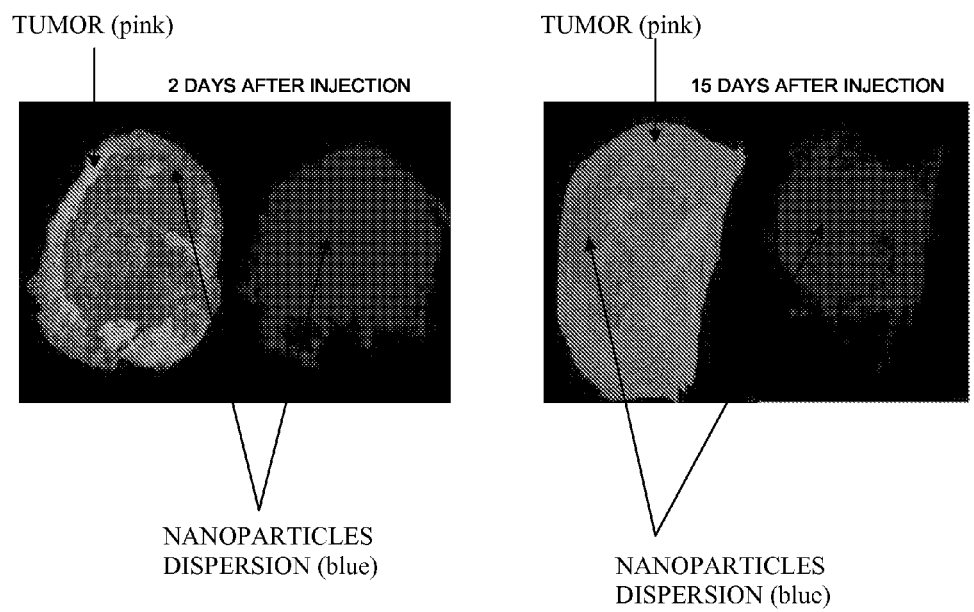
FIG. 1 shows the distribution and dispersion over time of biocompatible suspension of $HfO_2$ nanoparticles or nanoparticle aggregates after intra tumoral injection into Swiss nude mice bearing HCT116 tumor.

Nanoparticles dispersion after Intra-Tumor injection using nanoparticles biocompatible suspension from example 3 (FIG. 1):

Nanoparticle suspension has been intratumorously injected to Swiss nude mice bearing HCT116 tumor. The time residency of nanoparticles in tumor is at least 15 days, and no longer investigation has been possible due to sacrifice of mice required for ethical reasons. In addition, nanoparticles present a high contrast level and are easily detectable by X-Ray microtomography. Therefore, a microtomography has been performed 2 and 15 days after injection of nanoparticles in order to evaluate potential leakage of product from the tumor. It appears that distribution in tumour remains equivalent between 2 and 15 days and that the nanoparticles remain in the tumor (more than 15 days).

Example 8

Performance study of nanoparticles in HCT116 tumor model using nanoparticles from example 3 (FIGS. 6, 7 and 9):

Nanoparticles suspension has been intra-tumorously injected to Swiss nude mice bearing HCT116 tumors grafted on the flank. Local irradiation of tumor has been performed with an applicator coupled to an external irradiation using curietherapy device Iridium-192 sources. The position and the residence time of the Iridium-192 sources close to the tumor is optimized in order to deliver to the tumor an irradiation dose of 4 or 8 grays per fraction. A group of mice has been intra-tumorously injected with nanoparticles (injected volume is between 20% and 50% of the tumor volume) and submitted or not to two fractions of 4 Grays irradiations (24 and 48 hours after injection).

A second group has been intra-tumorously injected with nanoparticles (injected volume is between 20% and 50% of the tumor volume) and submitted or not to a single fraction of 8 Grays irradiations (24 hours after injection). The 4 groups of mice are compared to vehicle treated animals submitted or not to radiotherapy. Tumor volume is monitored in each group, twice a week. Nanoparticles lead to a total regression of tumor when compared to control mice submitted to radiotherapy alone. Evaluation on day 20 after irradiation showed an inhibition of tumor growth equal to 100% in nanoparticles treated mice after a 2×4 Grays or 1×8 Grays irradiation when compared to control submitted to radiotherapy alone with the same schedule.

Utilization of fractionated irradiation has proven a better benefit over risk ratio when compared to an irradiated reference group. In this context, a fractionated protocol using low doses of radiotherapy is possible. Such a protocol allows a better benefit over risk ratio when compared to regular radiotherapy protocol. Indeed such a fractionated protocol reduces the detrimental side effects which can be observed with conventional protocols on healthy tissues and is responsible for an equivalent or even better treatment efficacy.

Example 9

Clonogenic assay using biocompatible suspension of $HfO_2$ nanoparticles or nanoparticle aggregates from example 3, using either a 200 keV XRAY source (Tube Comet MXR-225/22-200 kV/15 mA/0.2 mm Cu) or a Cobalt 60 source (FIGS. 11A and 11B).

Materials and Method

Plating efficiency for HT1080 cancer cell line (radio resistant cancer cells) was determined before cell survival analysis or surviving fraction at x grays ($SF_x$). Cells were plated at a density to form between 50 and 200 colonies according to the treatment. When cells are attached, 400 µM of $HfO_2$ nanoparticles or nanoparticle aggregates from example 3 (with a density equal to 8.3 g/cm$^3$) are added with a maximum incubation time of 24 hours. Cell irradiation was performed using a 200 keV Irradiator (Tube Comet MXR-225/22-200 kV/15 mA/0.2 mm Cu) (FIG. 11A) and a Cobalt 60 source (FIG. 11B). After irradiation, cells were incubated for about 8 days at 37° C. before being fixed and stained with crystal violet solution. Only colonies comprising at least 50 cells were counted. $SF_x$ was determined using the following formula:

$SF_x$=[(number of colonies) at x dose/(total number of cells plated) at x dose]×plating efficiency Results: Effect of Irradiation on Radioresistant Cells As shown in FIGS. 11A and 11B, treatment of cancer cells with $HfO_2$ nanoparticles or nanoparticle aggregates from example 3 (density equal to 8.3), results in a significant increase in the level of radiation induced cell death in radio resistant (HT1080) cancer cells irradiated with a 200 keV Irradiator (Tube Comet MXR-225/22-200 kV/15 mA/0.2 mm Cu) or with a cobalt 60 source.

Results indicate the radiation enhancement ratio (ER) of the nanoparticles. HT1080 cells showed an ER of 1.38 for the 4-Gy dose alone with a 200 keV source (Tube Comet MXR-225/22-200 kV/15 mA/0.2 mm Cu) and an ER of 1 for the equivalent dose is observed when using a cobalt 60 source. These data demonstrate that nanoparticles are responsible for an advantageous clonogenic inhibition of irradiated radioresistant HT1080 cell lines using either a low ionizing radiation energy source or a high ionizing radiation energy source.

The above results demonstrate the efficacy of biocompatible oxide nanoparticles or nanoparticle aggregates with a density above 7 g/cm$^3$ to induce the death of cells (even of radioresistant cells) which have been irradiated with an energy radiation source, in particular a high energy radiation source.

Example 10

Effect of the Density of Biocompatible Oxide Nanoparticles or Nanoparticle Aggregates On Cell Viability WST-1 assay allows nanoparticles or nanoparticles aggregates screening of efficacy based on cell viability. Biocompatible inorganic nanoparticles or nanoparticle aggregates of distinct densities are herein tested.

Cell viability is measured after a 24 h-treatment period, with nanoparticles (800 µM down to 3.125 µM) or without nanoparticles, under fixed irradiation dose (2 Gy) using a 200 keV source (Tube Comet MXR-225/22-200 kV/15 mA/0.2 mm Cu), followed by a post incubation period of 96 hours.

The biocompatible oxide nanoparticles or nanoparticle aggregates cell viability is determined after a 2 Gy irradiation using said nanoparticles or nanoparticle aggregates (400 µM) and a fitting curve (cf. FIGS. 12A to L).

A decrease of cell viability superior to 20% (>20%) at 400 µM when compared with a radiotherapetic treatment alone (without nanoparticles) is considered as relevant. Indeed, when said biocompatible nanoparticles or nanoparticle aggregates are engaged in clonogenic assays, they allow a radiation enhancement ratio (ER) of 1.33 on HCT116 cell lines and of 1.60 on HT29 cell lines (cf. example 5).

A contrario, a decrease of cell viability inferior or equal to 20% (≤20%) at 400 µM when compared with a radiotherapeutic treatment alone (without nanoparticles) is considered as not relevant. Indeed, when said biocompatible nanoparticles or nanoparticle aggregates are engaged in clonogenic assays, irradiation had almost no significant effect on both the radio sensitive (HCT116) and radio resistant (HT29) cancer cells (cf. example 4).

The description of methods to prepare different tested oxides is reported in points a) to d). Commercial nanoparticles are described in point e). Density values, cell viability at 400 µM (when compared to a radiotherapeutic treatment alone) and relative efficiency at 800 µM, are reported in the below tables (see points a) to e)).

FIG. 12 present the cell viability (% of control) after a 2 Gy irradiation using nanoparticles or nanoparticle aggregates.

As explained previously, FIG. 13 presents the relative efficiency (ability to induce cell death), expressed as a percentage. Said relative efficiency reflects the cell viability (% of control), after a 2 Gy irradiation of the particles tested in example 10, at 800 µM, when compared to radiotherapeutic treatment alone (without nanoparticles), relatively to the cell viability (% of control) of biocompatible $HfO_2$ nanoparticles or nanoparticle aggregates (cf. example 3), at 800 µM, when compared to radiotherapeutic treatment alone (without nanoparticles).

In vitro efficiency assays conducted in this study highlight the importance of the density of the oxide with a threshold effect for d≥7 g/cm$^3$ (cf. FIG. 13).

Two groups of nanoparticles with significant differences in term of efficiency are distinguished:
  density<7 g/cm$^3$: the relative efficiency of the tested nanoparticles is below about 55%
  density≥7 g/cm$^3$: the relative efficiency of the tested nanoparticles is superior to about 80%.

a) Biocompatible Suspension of Hafnium Oxide ($HfO_2$) Nanoparticles or Nanoparticle Aggregates with a Density Ranging from 6.7 up to 8.3 g/cm$^3$, Using Sodium Hexametaphosphate as a Coating Agent A tetramethylammonium hydroxyde (TMAOH) solution is added to 40 g of $HfCl_4$ solution. Addition of TMAOH solution is performed until the pH of the final suspension reaches the desired pH value as reported in Table 2.

A white precipitate is obtained.

The precipitate is further transferred in an autoclave and heated at a temperature comprised between 120° C. and 300° C. to perform crystallization. After cooling, the suspension is washed with de-ionized water.

A peptization step is performed in order to get a stable suspension of nanoparticles or nanoparticle aggregates.

Suspension of sodium hexametaphosphate is then added to the peptized solution (the amount of added sodium hexametaphosphate being below LD50/5) and the pH of the suspension is adjusted in order to be comprised between about 6.5 and 7.5.

As apparent from the following Table 2 the density of the $HfO_2$ nanoparticles can be modulated with a careful adjustment of the pH of the initial suspension. Data regarding viability of irradiated cells exposed to each of the oxides of Table 2 appear respectively on FIGS. 12A, 12B and 12C.

TABLE 2

| Oxide | pH | density | cell viability (% of control) observed with an oxide concentration of 400 μM when compared with a radiotherapeutic treatment alone | Relative efficiency observed with an oxide concentration of 800 μM |
|---|---|---|---|---|
| HfO$_2$ Ref. example 3 | | 8.3 | >20% | 100% |
| HfO$_2$-L | pH 7 | 7.4 | 39% (HfO$_2$ ref.: 40%) | 97% |
| HfO2-E | pH 3 | 6.8 | 16% (HfO$_2$ ref.: 35%) | 53% |
| HfO2-V | pH2 | 6.7 | 9% (HfO$_2$ ref.: 43%) | 30% | b) Biocompatible Suspension of Cerium Oxide (CeO$_2$) Nanoparticles or Nanoparticles Aggregates with a Density Ranging from 6.5 up to 7.1, Using Sodium Hexametaphosphate as Coating Agent CeO$_2$ synthesis is adapted from Zhou & Al., Chem Mater, 2003, 15, 378-382.

Ce(SO$_4$)$_2$.4H$_2$O is dissolved in de-ionized water to obtain a 0.4 M solution. Ammonia solution is then added drop-wise at room temperature under continuous stirring. Ammonium solution is added to reach a final volume ratio of ammonium solution over cerium sulfate solution of 1:5. The resulting suspension is then washed by centrifugation 4 times with de-ionized water.

Final pellet is suspended in de-ionized water to get a solution of cerium oxide precursors of 0.05 M (CeO$_2$-1) or 0.2 M (CeO$_2$-2) both at pH 4. Solutions CeO$_2$-1 and CeO$_2$-2 are submitted to hydrothermal treatment at 180° C. during 24 hours. Samples are then washed 4 times with de-ionized water by centrifugation. Each sample is ultimately dried at 105° C. and submitted to a thermal treatment. Sample CeO$_2$-1 is calcined at 700° C. for 1 hour and CeO$_2$-2 at 900° C. for 1 hour to obtain respectively samples CeO$_2$-S and CeO$_2$-W.

A peptization step is performed in order to get a stable suspension of nanoparticles or nanoparticle aggregates.

Suspension of sodium hexametaphosphate is then added to the peptized solution (the amount of added sodium hexametaphosphate being below LD50/5) and the pH of the suspension is adjusted in order to be comprised between 6.5 and 7.5.

As apparent from the following Table 3 the density of the CeO$_2$ nanoparticles can be modulated with a careful adjustment of both temperature and duration of the thermal treatment. Data regarding viability of irradiated cells exposed to each of the oxides of Table 3 appear respectively on FIGS. 12D and 12E.

TABLE 3

| Oxide | Temperature and duration of calcination | density | cell viability (% of control) observed with an oxide concentration of 400 μM when compared with a radiotherapeutic treatment alone | Relative efficiency observed with an oxide concentration of 800 μM |
|---|---|---|---|---|
| HfO$_2$ Ref. Example 3 | | 8.3 | >20% | 100% |
| CeO$_2$—W | 900° C. 1 h | 7.1 | 30% (HfO$_2$ Ref.: 48%) | 91% |
| CeO$_2$—S | 700° C. 1 h | 6.5 | 20% (HfO$_2$ Ref.: 35%) | 56% | c) Biocompatible Suspension of Thulium Oxide (Tm$_2$O$_3$) Nanoparticles or Nanoparticles Aggregates with a Density Ranging from 2.7 up to 8.3 g/cm$^3$ 5 g of TmCl$_3$ are dissolved in HCl 2M. A tetramethylammonium hydroxide (TMAOH) solution is then added to the TmCl$_3$ solution until pH is at 7 (Tm$_2$O$_3$-0) or 8 (Tm$_2$O$_3$-1). A white precipitate is obtained.

The precipitate is submitted to hydrothermal treatment in autoclave, i.e., is heated at a temperature between 120° C. and 300° C. The resulting suspension is then washed by centrifugation with de-ionized water and dried at 105° C. overnight.

Powders are submitted to calcinations:
Tm$_2$O$_3$: 400° C., 1 h
Tm$_2$O$_3$: 600° C., 1 h
Tm$_2$O$_3$: 800° C., 5 mn
Tm$_2$O$_3$: 800° C., 2 h As apparent from the following Table 4 the density of the Tm$_2$O$_3$ nanoparticles can be modulated with a careful adjustment of both temperature and duration of the thermal treatment.

TABLE 4

| Oxide | Temperature and duration of calcination | density |
|---|---|---|
| Tm$_2$O$_3$ | 800° C. 2 h | 8.3 |
| Tm$_2$O$_3$ | 800° C. 5 mn | 6.8 |
| Tm$_2$O$_3$ | 600° C. 1 h | 6.1 |
| Tm2O3 | 400° C. 1 h | 4.9 |
| Tm$_2$O$_3$-1 | none | 2.7 | d) Biocompatible Suspension of Titanium Oxide (TiO$_2$) Nanoparticles or Nanoparticle Aggregates with a Density Below 7 g/cm$^3$, Using Sodium Hexametaphosphate as a Coating Agent.

15 mL of TiCl$_4$ are added drop-wise in 180 mL of HCl 3M solution under gentle agitation. 120 mL of de-ionized water is further added to get a final volume of 215 mL. The pH of the solution is progressively adjusted to 2 using NaOH 3 M solution. Solution turned to a white precipitate which is heated at 60° C. during 24 h. A peptization step is performed in order to get a stable suspension of nanoparticles or nanoparticles aggregates.

Suspension of sodium hexametaphosphate is then added to the peptized solution (the amount of added sodium hexametaphosphate being below LD50/5) and the pH of the suspension is adjusted in order to be comprised between 6.5 and 7.5.

Data regarding viability of irradiated cells exposed to TiO$_2$ oxide of Table 5 appear on FIG. 12F.

TABLE 5

| Oxide | density | cell viability (% of control) observed with an oxide concentration of 400 μM when compared with a radiotherapeutic treatment alone | Relative efficiency observed with an oxide concentration of 800 μM |
|---|---|---|---|
| HfO$_2$ Ref. Example 3 | 8.3 | >20% | 100% |
| TiO$_2$_5 nm | 3.9 | 11% (HfO$_2$ Ref.: 49%) | 48% | e) Biocompatible Suspension of Commercial Oxide Nanoparticles or Nanoparticle Aggregates with a Density Ranging from 3.8 up to 7.9, Using Sodium Hexametaphosphate as Coating Agent.

All oxide nanoparticles of nanoparticle aggregates are obtained as commercial powders (highest purity grade).

The powders are dispersed in aqueous solution and submitted to ultrasounds for efficient dispersion in solution.

A peptization step is performed in order to get a stable suspension of nanoparticles or nanoparticle aggregates.

Suspension of sodium hexametaphosphate is then added to the peptized solution (the amount of sodium hexametaphosphate added being below LD50/5) and the pH of the suspension is adjusted in order to be comprised between 6.5 and 7.5.

Data regarding viability of irradiated cells exposed to each of the oxides of Table 6 appear respectively on FIGS. 12G, 12H, 12I, 12J, 12K and 12L.

TABLE 6

| Oxide | Density | cell viability (% of control) observed with an oxide concentration of 400 μM when compared with a radiotherapeutic treatment alone | Relative efficiency observed with an oxide concentration of 800 μM |
|---|---|---|---|
| $HfO_2$ Ref. Example 3 | 8.3 | >20% | 100% |
| PdO-A | 7.9 | 34% ($HfO_2$ Ref.: 48%) | 79% |
| $TiO_2$-P25 | 3.8 | 12% ($HfO_2$ Ref.: 49%) | <25% |
| $CeO_2$-D | 6.6 | 12% ($HfO_2$ Ref.: 24%) | 42% |
| $Nd_2O_3$-Z | 5.4 | <10% ($HfO_2$ Ref.: 33%) | <25% |
| $Eu_2O_3$-B | 5.6 | <10% ($HfO_2$ Ref.: 21%) | <25% |
| $WO_3$-C | 7.2 | 40.5% ($HfO_2$ Ref.: 42%) | 95% |

Example 11

Importance of a Biocompatible Surface Coating for Efficient Stability of Titanium Oxide ($TiO_2$), Cerium Oxide ($CeO_2$) and Hafnium Oxide ($HfO_2$) Nanoparticles or Nanoparticles Aggregates Suspension, Using Sodium Hexametaphosphate as a Coating Agent In order to be used in vivo, activable nanoparticles or nanoparticle aggregates must be biocompatible. Biocompatibility requires high stability in physiological media ($6.5 \leq pH \leq 7.5$) to avoid aggregation in blood circulation and to allow for an efficient biodistribution (EPR effect). Hence, a pre-requisite prior injection is to check the stability of the nanoparticle or nanoparticle aggregate suspension in physiological conditions.

We thus evaluated particles stability with or without HMP coating in water and glucose (5%). Stability was confirmed visually in the different media and by filtration yield using a 0.22 μm filter.

Results: Stability

Nanoparticles suspensions ($TiO_2$-5 nm from example 10d), commercial $CeO_2$-D from example 10e) and $HfO_2$-Ref. from example 3)—peptized suspension at pH3 or suspension at pH 7—without HMP as a biocompatible surface coating agent, are formulated in glucose solution (5%). Nanoparticles suspensions at pH 7 with HMP coating are also formulated in glucose solution (5%). Concentration of nanoparticles for each suspension is at about 5 g/L. Each sample are let 2 h and a first discriminating analysis of nanoparticles stability in suspension is performed visually (FIG. 14).

This first evaluation shows that all uncoated samples remain stable at pH 3 in water and glucose solution (5%) due to the presence of positive charges on the particles surface since all the particles have an isoelectric point (IEP) close to pH 6-7.

By increasing the pH of the suspension (water or glucose) up to 7, precipitation of nanoparticles is observed, the pH being close to the IEP. Particles coating using HMP increase drastically stability at pH 7 in water and glucose solution (5%).

Results: Yield of Filtration 0.22 μm cutoff filters authorize the passage of only well dissociated nanoparticles or nanoparticle aggregates. Even if very few aggregations occur, particles will accumulate on the filter and quickly block the filter. Particles concentration was estimated via balance sheet prior and after filtration.

The data presented on FIG. 15 demonstrate the role of biocompatible coating which is absolutely necessary to improve the nanoparticle surface properties and to improve particles stability under physiological conditions.

The invention claimed is:

1. A method for altering, destroying or eliminating target cells in an animal by i) administering a nanoparticle or nanoparticle aggregate or a composition comprising the nanoparticle or nanoparticle aggregate, wherein the nanoparticle or nanoparticle aggregate consists of a metal oxide coated with a biocompatible coating, wherein the density of the nanoparticle or the density of the nanoparticle aggregate is at least 7 g/cm$^3$, and the nanoparticle or nanoparticle aggregate is covered with a biocompatible coating providing the nanoparticle or the nanoparticle aggregate stability between pH 6.5 and 7.5 in a physiological fluid, and ii) exposing said animal to ionizing radiations.

2. The method according to claim 1, wherein the metal oxide is selected from the group consisting of $CeO_2$, $Nd_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Lu_2O_3$, $HfO_2$, $TaO_2$, $Ta_2O_5$, $WO_2$, $WO_3$, $ReO_2$, $OsO_2$, $IrO_2$, $PtO$, $PtO_2$, $HgO$, $Hg_2O$, $Tl_2O_3$, $PbO$, $Pb_2O_3$, $Pb_3O_4$, $PbO_2$, $PoO_2$, $Bi_2O_3$, $NbO$, $RuO_2$, $Rh_2O_3$, $RhO_2$, $PdO$, $Ag_2O$, $AgO$, $CdO$, and $In_2O_3$.

3. The method according to claim 2, wherein the metal oxide is $HfO_2$.

4. The method according to claim 1, wherein the size of the nanoparticle or nanoparticle aggregate is between around 10 and 200 nm.

5. The method according to claim 1, wherein said ionizing radiations are selected from the group consisting of X-Rays, γ-Rays, electron beams and radioisotope emissions.

6. The method according to claim 1, wherein the ionizing radiations are of about 2 KeV to about 25 000 KeV.

7. The method according to claim 6, wherein the ionizing radiations are of about 2 KeV to 6000 KeV.

8. The method according to claim 6, wherein the ionizing radiations are of about 2 KeV to 1500 KeV.

9. The method according to claim 1, wherein the nanoparticle or nanoparticle aggregate consists of a metal oxide having an effective atomic number ($Z_{eff}$) of at least 50.

10. The method according to claim 1, wherein the nanoparticle or nanoparticle aggregate is essentially spherical in shape.

11. The method according to claim 1, wherein target cells are selected in the group consisting of benign cells, premalignant cells and malignant cells.

12. The method according to claim 11, wherein said malignant cells are cells from a tumor selected from the group consisting of a hematological tumor and a solid tumor.

13. The method according to claim 1, wherein the pharmaceutical composition further comprises an additional therapeutic anti-cancer compound, said therapeutic compound being distinct from said nanoparticle or nanoparticle aggregate.

14. The method according to claim 1, wherein said animal is a human.

15. A pharmaceutical composition for altering, destroying, or eliminating target cells in a mammal when said cells are exposed to ionizing radiations, said pharmaceutical composition comprising a nanoparticle or nanoparticle aggregate and a pharmaceutically acceptable excipient, wherein the nanoparticle or nanoparticle aggregate consists of a metal oxide coated with a biocompatible coating, the density of the nanoparticle or the density of the nanoparticle aggregate is of at least 7 g/cm$^3$, and the nanoparticle or nanoparticle aggregate is covered with a biocompatible coating providing the nanoparticle or nanoparticle aggregate stability between pH 6.5 and 7.5 in a physiological fluid.

16. A pharmaceutical composition comprising a nanoparticle or nanoparticle aggregate and a pharmaceutically acceptable excipient, wherein the nanoparticle or nanoparticle aggregate consists of a metal oxide coated with a biocompatible coating, the density of the nanoparticle or the density of the nanoparticle aggregate being at least 7 g/cm$^3$ and less than 15 g/cm$^3$, the nanoparticle or nanoparticle aggregate being covered with a biocompatible coating providing stability between pH 6.5 and 7.5 in a physiological fluid.

17. The method according to claim 1, wherein said biocompatible coating is selected from the group consisting of an inorganic agent, a metallic agent, an organic agent, and mixtures or combinations thereof.

18. The method according to claim 17, wherein said is selected from the group consisting of an oxide, an hydroxide, an oxyhydroxide and mixtures or combinations thereof.

19. The method according to claim 18, wherein the oxide, hydroxide or oxyhydroxide contains silicium, aluminum, zirconium, calcium, magnesium and/or tin.

20. The method according to claim 17, wherein said biocompatible coating is gold, silver or platinum.

21. The method according to claim 17, wherein said biocompatible coating is a polyethylene glycol (PEG), polyethylenoxide, polyvinylalcohol, polyacrylate, polyacrylamide (poly(N-isopropylacrylamide)), polycarbamide, dextran, xylan, cellulose, collagen, or a zwitterionic compound.

22. The method according to claim 17, wherein said biocompatible coating is sodium trimetaphosphate (STMP) or sodium hexametaphosphate (HMP).

* * * * *

UNITED STATES PATENT AND TRADEMARK OFFICE
CERTIFICATE OF CORRECTION

PATENT NO. : 8,845,507 B2  Page 1 of 1
APPLICATION NO. : 12/994162
DATED : September 30, 2014
INVENTOR(S) : Laurent Levy et al.

It is certified that error appears in the above-identified patent and that said Letters Patent is hereby corrected as shown below:

In The Specification

Column 9,
Line 22, "density 7 g/cm$^3$:" should read --density $\geq$ 7 g/cm$^3$:--.

Column 10,
Line 62, "(MA)" should read --($M_xO_y$)--.

Column 18,
Line 3, "comprises" should read --comprise--.

Column 20,
Line 39, "25 Mev." should read --25 MeV.--.
Lines 40-41, "used for selectively" should read --used to selectively--.
Line 41, "X-rays radiation" should read --X-ray radiation--.

Column 21,
Line 15, "as cating agent." should read --as coating agent.--.

Column 28,
Line 27, "Tm2O3" should read --$Tm_2O_3$--.

In The Claims

Column 32,
Line 5, "said is" should read --said inorganic agent is--.

Signed and Sealed this
Twenty-eighth Day of April, 2015

Michelle K. Lee
*Director of the United States Patent and Trademark Office*